United States Patent
Warnatz et al.

(10) Patent No.: US 9,631,214 B2
(45) Date of Patent: Apr. 25, 2017

(54) METHOD FOR LINKING AND CHARACTERISING LINKED NUCLEIC ACIDS, E.G. ANTIBODY ENCODING NUCLEIC ACIDS, IN A COMPOSITION

(71) Applicants: MAX-PLANCK GESELLSCHAFT ZUR FOERDERUNG DER WISSSENSCHAFTEN E.V., Munich (DE); ALACRIS THERANOSTICS GMBH, Berlin (DE)

(72) Inventors: Hans-Joerg Warnatz, Berlin (DE); Joern Gloekler, Berlin (DE); Hans Lehrach, Berlin (DE)

(73) Assignees: Max-Planck Gesellschaft Zur Foerderung Der Wissenschaften E.V., Munich (DE); Alaeris Theranostics GmbH, Berlin (DE)

( * ) Notice: Subject to any disclaimer, the term of this patent is extended or adjusted under 35 U.S.C. 154(b) by 0 days.

(21) Appl. No.: 14/377,358

(22) PCT Filed: Feb. 6, 2013

(86) PCT No.: PCT/EP2013/052328
§ 371 (c)(1),
(2) Date: Aug. 7, 2014

(87) PCT Pub. No.: WO2013/117591
PCT Pub. Date: Aug. 15, 2013

(65) Prior Publication Data
US 2015/0004618 A1    Jan. 1, 2015

(30) Foreign Application Priority Data
Feb. 9, 2012 (EP) .................... 12154726

(51) Int. Cl.
C12P 19/34 (2006.01)
C12Q 1/68 (2006.01)
C07K 16/00 (2006.01)
C12P 21/08 (2006.01)

(52) U.S. Cl.
CPC .............. *C12P 19/34* (2013.01); *C07K 16/00* (2013.01); *C12Q 1/6858* (2013.01); *C12Q 1/6869* (2013.01); *C12Q 1/6876* (2013.01); *C07K 2317/14* (2013.01); *C12Q 2525/161* (2013.01); *C12Q 2600/156* (2013.01)

(58) Field of Classification Search
None
See application file for complete search history.

(56) References Cited

U.S. PATENT DOCUMENTS

2010/0261189 A1 * 10/2010 Bentley et al. .................... 435/6

FOREIGN PATENT DOCUMENTS

| EP | 1 516 929 | 3/2005 | |
| WO | WO 93/03151 | 2/1993 | |
| WO | WO 2008/005675 | 1/2008 | |
| WO | WO 2008/104184 | * 9/2008 | ............. C12N 15/10 |
| WO | WO 2009/049889 | 4/2009 | |

OTHER PUBLICATIONS

Fujiki et al., "Isolation of Intracellular Membranes by Means of Sodium Carbonate Treatment: Application to Endoplasmic Reticulum" 93 The Journal of Cell Biology 97-102 (1982).*
Glanville et al., "Precise determination of the diversity of a combinatorial antibody library gives insight into the human immunoglobulin repertoire" 106(48) Proceedings of the National Academy of Sciences USA 10116-20221 (2009).*
Siekevitz, "Protoplasm: Endoplasmic Reticulum Microsomes and Their Properties" 25 Annual Review of Physiology 15-40 (1963).*
Angenendt Phillip et al. "Cell-free Protein Expression and Functional Assay in Nanowell Chip Format" Analytical Chemistry, vol. 76, No. 7, pp. 1844-1849 Apr. 1, 2004.
Saggy, Ido et al. "Antibody isolation from immunized animals: comparison of phage display and antibody discovery via V gene repertoire mining", Protein Engineering, Design and Selection vol. 25, No. 10 pp. 539-549, 2012.
Smith, Andrew M. et al. "Highly-multiplexed barcode sequencing: an efficient method for parallel analysis of pooled samples", Nucleic Acids Research, 2010, 1-7.
Hanes, Jozef et al. "In vitro selection and evolution of functional proteins by using ribosome display", Proc. Natl. Acad. Sci USA vol. 94, pp. 4937-4942, May 1997.
Tiller, Thomas et al. "Efficient generation of monoclonal antibodies from single human B cells by single cell RT-PCR and expression vector cloning", J Immunol Methods, Jan. 1, 2008: 329(1-2): 112-124.
Brand, Korbinian et al. "A novel A—G mutation in intron I of the hepatic lipase gene leads to alternative splicing resulting in enzyme defieciency", Journal of Lipid Research vol. 37, pp. 1213-1223, 1996
Wang, M et al. "Sequence analysis of the late region of human papillomavirus type 6 genome", ZhongguoYl Xue Ke Xue Yuan Xue Bao, Dec. 2001; 23(6) 568-72.

* cited by examiner

*Primary Examiner* — Nancy J Leith
(74) *Attorney, Agent, or Firm* — Ballard Spahr LLP

(57) ABSTRACT

The invention relates to a method for linking at least two target nucleic acid molecules from a single biological compartment, comprising the steps of isolating a fraction from a sample, wherein the fraction comprises the compartment comprising at least two nucleic acid molecules, diluting the fraction and aliquoting the dilution in multiple separate reaction vessels such that each reaction vessel comprises preferably one compartment, or encapsulating the compartment in emulsion droplets such that each droplet comprises preferably one compartment; linking the at least two target nucleic acid molecules, preferably by overlap extension PCR. The method may be employed in the analysis of mutations present in a single cell and in the production of antibodies which are present in a single hybridoma.

11 Claims, 3 Drawing Sheets

SEQUENCE LISTING

<160> NUMBER OF SEQ ID NOS: 41

<210> SEQ ID NO 1
<211> LENGTH: 48
<212> TYPE: DNA
<213> ORGANISM: Artificial Sequence
<220> FEATURE:
<223> OTHER INFORMATION: Primer

<400> SEQUENCE: 1
cgtatcgcct ccctcgcgcc atcagtgatt gtcttttgtc aggggtct                    48

<210> SEQ ID NO 2
<211> LENGTH: 48
<212> TYPE: DNA
<213> ORGANISM: Artificial Sequence
<220> FEATURE:
<223> OTHER INFORMATION: Primer

<400> SEQUENCE: 2
cgtatcgcct ccctcgcgcc atcagtgatt gtcttttgtt aggggtcg                    48

<210> SEQ ID NO 3
<211> LENGTH: 47
<212> TYPE: DNA
<213> ORGANISM: Artificial Sequence
<220> FEATURE:
<223> OTHER INFORMATION: Primer

<400> SEQUENCE: 3
tcgtgcctat atccttactg actctgcgga acacagtggt gcctacc                     47

<210> SEQ ID NO 4
<211> LENGTH: 47
<212> TYPE: DNA
<213> ORGANISM: Artificial Sequence
<220> FEATURE:
<223> OTHER INFORMATION: Primer

<400> SEQUENCE: 4
tcgtgcctat atccttactg actctgcgga acactgtggt acccacc                     47

<210> SEQ ID NO 5
<211> LENGTH: 50
<212> TYPE: DNA
<213> ORGANISM: Artificial Sequence
<220> FEATURE:
<223> OTHER INFORMATION: Primer

<400> SEQUENCE: 5
gcagagtcag taaggatata ggcacgatcc aattcaaggt aatcagatgc                  50

<210> SEQ ID NO 6
<211> LENGTH: 48
<212> TYPE: DNA
<213> ORGANISM: Artificial Sequence
<220> FEATURE:
<223> OTHER INFORMATION: Primer

<400> SEQUENCE: 6
ctatgcgcct tgccagcccg ctcagcccaa gaggaaacac tctaggac                    48

<210> SEQ ID NO 7
<211> LENGTH: 48
<212> TYPE: DNA
<213> ORGANISM: Artificial Sequence

```
<220> FEATURE:
<223> OTHER INFORMATION: Primer

<400> SEQUENCE: 7
ctatgcgcct tgccagcccg ctcagcccaa gaggaaacac actaggtc          48

<210> SEQ ID NO 8
<211> LENGTH: 21
<212> TYPE: DNA
<213> ORGANISM: Artificial Sequence
<220> FEATURE:
<223> OTHER INFORMATION: Primer

<400> SEQUENCE: 8
ggacggggaa cgacaattac c                                       21

<210> SEQ ID NO 9
<211> LENGTH: 28
<212> TYPE: DNA
<213> ORGANISM: Artificial Sequence
<220> FEATURE:
<223> OTHER INFORMATION: Primer

<400> SEQUENCE: 9
cacactaggt cgtggaacaa caattact                                28

<210> SEQ ID NO 10
<211> LENGTH: 31
<212> TYPE: DNA
<213> ORGANISM: Artificial Sequence
<220> FEATURE:
<223> OTHER INFORMATION: Primer

<400> SEQUENCE: 10
aacagttggt tgattatcag aagctgtaga a                            31

<210> SEQ ID NO 11
<211> LENGTH: 22
<212> TYPE: DNA
<213> ORGANISM: Artificial Sequence
<220> FEATURE:
<223> OTHER INFORMATION: Primer

<400> SEQUENCE: 11
ctgattatcg gaagccgtgg ag                                      22

<210> SEQ ID NO 12
<211> LENGTH: 49
<212> TYPE: DNA
<213> ORGANISM: Artificial Sequence
<220> FEATURE:
<223> OTHER INFORMATION: Primer

<400> SEQUENCE: 12
cgtatcgcct ccctcgcgcc atcaggacat ttgggaagga ctgactctc         49

<210> SEQ ID NO 13
<211> LENGTH: 47
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (33)..(33)
<223> OTHER INFORMATION: n is a, c, g, or t
```

<400> SEQUENCE: 13
tcgtgcctat atccttactg actctgcsar gtnmagctgs agsagtc          47

<210> SEQ ID NO 14
<211> LENGTH: 51
<212> TYPE: DNA
<213> ORGANISM: Artificial Sequence
<220> FEATURE:
<223> OTHER INFORMATION: Primer

<400> SEQUENCE: 14
gcagagtcag taaggatata ggcacgagay attgtgmtsa cmcarwctmc a     51

<210> SEQ ID NO 15
<211> LENGTH: 47
<212> TYPE: DNA
<213> ORGANISM: Artificial Sequence
<220> FEATURE:
<223> OTHER INFORMATION: Primer

<400> SEQUENCE: 15
ctatgcgcct tgccagcccg ctcagggata cagttggtgc agcatca          47

<210> SEQ ID NO 16
<211> LENGTH: 25
<212> TYPE: DNA
<213> ORGANISM: Artificial Sequence
<220> FEATURE:
<223> OTHER INFORMATION: Primer

<400> SEQUENCE: 16
cgtatcgcct ccctcgcgcc atcag                                  25

<210> SEQ ID NO 17
<211> LENGTH: 25
<212> TYPE: DNA
<213> ORGANISM: Artificial Sequence
<220> FEATURE:
<223> OTHER INFORMATION: Primer

<400> SEQUENCE: 17
ctatgcgcct tgccagcccg ctcag                                  25

<210> SEQ ID NO 18
<211> LENGTH: 27
<212> TYPE: DNA
<213> ORGANISM: Artificial Sequence
<220> FEATURE:
<223> OTHER INFORMATION: Primer

<400> SEQUENCE: 18
tcgtgcctat atccttactg actctgc                                27

<210> SEQ ID NO 19
<211> LENGTH: 27
<212> TYPE: DNA
<213> ORGANISM: Artificial Sequence
<220> FEATURE:
<223> OTHER INFORMATION: Primer

<400> SEQUENCE: 19
gcagagtcag taaggatata ggcacga                                27

-continued

```
<210> SEQ ID NO 20
<211> LENGTH: 59
<212> TYPE: DNA
<213> ORGANISM: Artificial Sequence
<220> FEATURE:
<223> OTHER INFORMATION: Primer

<400> SEQUENCE: 20
cgtatcgcct ccctcgcgcc atcagagacg cactcgacat ttgggaagga ctgactctc      59

<210> SEQ ID NO 21
<211> LENGTH: 47
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (33)..(33)
<223> OTHER INFORMATION: n = a, t, g or c

<400> SEQUENCE: 21
tcgtgcctat atccttactg actctgcsar gtnmagctgs agsagtc                   47

<210> SEQ ID NO 22
<211> LENGTH: 51
<212> TYPE: DNA
<213> ORGANISM: Artificial Sequence
<220> FEATURE:
<223> OTHER INFORMATION: Primer

<400> SEQUENCE: 22
gcagagtcag taaggatata ggcacgagay attgtgmtsa cmcarwctmc a              51

<210> SEQ ID NO 23
<211> LENGTH: 57
<212> TYPE: DNA
<213> ORGANISM: Artificial Sequence
<220> FEATURE:
<223> OTHER INFORMATION: Primer

<400> SEQUENCE: 23
ctatgcgcct tgccagcccg ctcagtactg agctaggata cagttggtgc agcatca       57

<210> SEQ ID NO 24
<211> LENGTH: 24
<212> TYPE: DNA
<213> ORGANISM: Artificial Sequence
<220> FEATURE:
<223> OTHER INFORMATION: Primer

<400> SEQUENCE: 24
gatctgcaag agatggaggc ttga                                            24

<210> SEQ ID NO 25
<211> LENGTH: 22
<212> TYPE: DNA
<213> ORGANISM: Artificial Sequence
<220> FEATURE:
<223> OTHER INFORMATION: Primer

<400> SEQUENCE: 25
cctgcaggtc atggtgacct tt                                              22
```

<210> SEQ ID NO 26
<211> LENGTH: 22
<212> TYPE: DNA
<213> ORGANISM: Artificial Sequence
<220> FEATURE:
<223> OTHER INFORMATION: Primer

<400> SEQUENCE: 26
gcatggcaag tgatgctgac tg                                              22

<210> SEQ ID NO 27
<211> LENGTH: 23
<212> TYPE: DNA
<213> ORGANISM: Artificial Sequence
<220> FEATURE:
<223> OTHER INFORMATION: Primer

<400> SEQUENCE: 27
gcggacccag ttcatccagt agt                                             23

<210> SEQ ID NO 28
<211> LENGTH: 25
<212> TYPE: DNA
<213> ORGANISM: Artificial Sequence
<220> FEATURE:
<223> OTHER INFORMATION: Primer

<400> SEQUENCE: 28
tgttttaccc agtgcatcca gtagg                                           25

<210> SEQ ID NO 29
<211> LENGTH: 22
<212> TYPE: DNA
<213> ORGANISM: Artificial Sequence
<220> FEATURE:
<223> OTHER INFORMATION: Primer

<400> SEQUENCE: 29
cgaacccaag acatggcata gc                                              22

<210> SEQ ID NO 30
<211> LENGTH: 58
<212> TYPE: DNA
<213> ORGANISM: Artificial Sequence
<220> FEATURE:
<223> OTHER INFORMATION: Primer

<400> SEQUENCE: 30
cgtatcgcct ccctcgcgcc atcagacgag tgcgtaaggg ttggggcgga tgcactcc       58

<210> SEQ ID NO 31
<211> LENGTH: 52
<212> TYPE: DNA
<213> ORGANISM: Artificial Sequence
<220> FEATURE:
<223> OTHER INFORMATION: Primer

<400> SEQUENCE: 31
tcgtgcctat atccttactg actctgcggc ctcagtgaag gtctcctgca ag             52

<210> SEQ ID NO 32
<211> LENGTH: 51
<212> TYPE: DNA
<213> ORGANISM: Artificial Sequence
<220> FEATURE:
<223> OTHER INFORMATION: Primer

<400> SEQUENCE: 32
tcgtgcctat atccttactg actctgcgtc tggtcctacg ctggtgaacc c       51

<210> SEQ ID NO 33
<211> LENGTH: 52
<212> TYPE: DNA
<213> ORGANISM: Artificial Sequence
<220> FEATURE:
<223> OTHER INFORMATION: Primer

<400> SEQUENCE: 33
tcgtgcctat atccttactg actctgcctg gggggtccct gagactctcc tg      52

<210> SEQ ID NO 34
<211> LENGTH: 52
<212> TYPE: DNA
<213> ORGANISM: Artificial Sequence
<220> FEATURE:
<223> OTHER INFORMATION: Primer

<400> SEQUENCE: 34
tcgtgcctat atccttactg actctgcctt cggagaccct gtccctcacc tg      52

<210> SEQ ID NO 35
<211> LENGTH: 52
<212> TYPE: DNA
<213> ORGANISM: Artificial Sequence
<220> FEATURE:
<223> OTHER INFORMATION: Primer

<400> SEQUENCE: 35
tcgtgcctat atccttactg actctgccgg ggagtctctg aagatctcct gt      52

<210> SEQ ID NO 36
<211> LENGTH: 52
<212> TYPE: DNA
<213> ORGANISM: Artificial Sequence
<220> FEATURE:
<223> OTHER INFORMATION: Primer

<400> SEQUENCE: 36
tcgtgcctat atccttactg actctgctcg cagaccctct cactcacctg tg      52

<210> SEQ ID NO 37
<211> LENGTH: 50
<212> TYPE: DNA
<213> ORGANISM: Artificial Sequence
<220> FEATURE:
<223> OTHER INFORMATION: Primer

<400> SEQUENCE: 37
gcagagtcag taaggatata ggcacgagac atccrgdtga cccagtctcc          50

<210> SEQ ID NO 38
<211> LENGTH: 52
<212> TYPE: DNA
<213> ORGANISM: Artificial Sequence
<220> FEATURE:
<223> OTHER INFORMATION: Primer

<400> SEQUENCE: 38
gcagagtcag taaggatata ggcacgaggg atattgtgmt gacycagwct cc      52

```
<210> SEQ ID NO 39
<211> LENGTH: 53
<212> TYPE: DNA
<213> ORGANISM: Artificial Sequence
<220> FEATURE:
<223> OTHER INFORMATION: Primer

<400> SEQUENCE: 39
gcagagtcag taaggatata ggcacgagga gaaattgtrw tgacrcagtc tcc         53

<210> SEQ ID NO 40
<211> LENGTH: 52
<212> TYPE: DNA
<213> ORGANISM: Artificial Sequence
<220> FEATURE:
<223> OTHER INFORMATION: Primer

<400> SEQUENCE: 40
gcagagtcag taaggatata ggcacgagca gaaacgacac tcacgcagtc tc          52

<210> SEQ ID NO 41
<211> LENGTH: 61
<212> TYPE: DNA
<213> ORGANISM: Artificial Sequence
<220> FEATURE:
<223> OTHER INFORMATION: Primer

<400> SEQUENCE: 41
ctatgcgcct tgccagcccg ctcagtactg agctagaaga cagatggtgc agccacagtt  60
c                                                                  61
```

US 9,631,214 B2

METHOD FOR LINKING AND CHARACTERISING LINKED NUCLEIC ACIDS, E.G. ANTIBODY ENCODING NUCLEIC ACIDS, IN A COMPOSITION

This application is a National Stage of PCT/EP2013/052328, filed Feb. 6, 2013 which claims priority to European Application No. 12154726.9, filed Feb. 9, 2012, the disclosures of which are incorporated herein by reference in their entirety.

FIELD OF THE INVENTION

The present invention is in the field of molecular biology, diagnostics and more in particular also medicine. It is also in the field of biochemistry and molecular biology.

The instant application contains a Sequence Listing which has been submitted in ASCII format via EFS-Web and is hereby incorporated by reference in its entirety. Said ASCII copy, created on Jul. 30, 2014, is named 01170001US1SL.txt and is 7.70 kilobytes in size.

BACKGROUND

It is difficult to determine the degree of variation on the level of single cells in a heterogeneous cell population for single-nucleotide polymorphisms (SNPs), variable sequence regions and splice variants. If bulk nucleic acids are isolated from cell populations, the information which nucleic acid variants were present in which combination in each individual cell is lost.

This information can be important in cases where different nucleic acid variants act together in cells to determine the specific biological behavior of the cells. For example, two mutations in two different signaling pathway molecules can result in malignancy of individual cancer cells, whereas other cells in the same tumor population that carry only one of these mutations are non-malignant. Other examples include the variable T cell receptor alpha and beta chain genes and transcripts, which act together in each T cell to produce T cell receptors that are variable among each T cell, and the immunoglobulin variable heavy chain (VH) and variable light chain (VL) genes and transcripts present in B cells, which act together in each B cell to produce immunoglobulins that are variable among each B cell.

Conventionally, combinations of nucleic acid variations can be analyzed after isolating single cells through simple titration, through cell picking or through fluorescence-activated cells sorting (FACS). Subsequently, the combinations of sequence variants can be analyzed after amplification of the nucleic acids of interest from each individual cell by polymerase chain reaction (PCR) or reverse transcription-PCR (RT-PCR). Analysis methods include nucleic acid sequencing, hybridization on microarrays or quantitative real-time PCR (qPCR). In order to facilitate the analysis of the pairing of nucleic acid variations, different gene sequences or reverse-transcribed RNA sequences can be coupled by overlap PCR, which has been reported to be compatible with water-in-oil emulsions. A method for coupling variable regions of immunoglobulin genes by multiplex overlap-extension RT-PCR from isolated single cells has been described before (U.S. Pat. No. 7,749,697B2). Similar methods have been used by others to clone functional antibody variable domains in the form of single-chain variable fragments (scFv) from natural repertoires such as hybridoma cells and spleen cells.

Another method for coupling of two or more copies of non-contiguous DNA sequences from single cells of a heterogeneous population has been described before (Patent EP597960B1). Gene elements can be coupled inside single cells (in situ "in-cell PCR") within intact or substantially intact cells after cell fixing e.g. with formaldehyde and subsequent cell permeabilization to ensure access of PCR reagents to the gene elements (Embleton M J, Gorochov G, Jones P T, Winter G. In-cell PCR from mRNA: amplifying and linking the rearranged immunoglobulin heavy and light chain V-genes within single cells. Nucleic Acids Res. 1992 Aug. 11; 20(15):3831-7). Alternatively, cells and PCR reagents can be introduced into aqueous droplets and dispersed in an organic phase as an emulsion, wherein each droplet contains preferentially only one cell, such that gene elements from single cells are coupled together.

The coupling of nucleic acids is a known technique and has been used for the analysis antibodies and their VH and VL genes. EP1516929 and WO2008/104184 describe methods for the analysis of specific antibodies, wherein nucleic acids from single cells were coupled. The coupled nucleic acids were cloned into expression vectors and specific antibodies were identified using ELISA assays, which were then optionally sequenced.

The methods allow the identification of specific antibodies against a particular antigen, possibly in a high throughput manner. However it is not suitable to determine the complete and complex immune status of an organism. Furthermore for the analysis of specific antibodies the method involves FACS sorting, which requires expensive equipment and is time consuming.

The methods however are tedious.

The technical problem underlying the present invention is the provision of an enhanced method that facilitates the analysis of nucleic acid molecules in cases where these molecules act together in a cell.

The technical problem is solved by the embodiments provided herein and as described by the claims, specifically by a method for linking at least two target nucleic acid molecules from a single biological compartment, comprising the steps of isolating a fraction from a sample, wherein the fraction comprises the compartment comprising at least two nucleic acid molecules; diluting said fraction and aliquoting the dilution in multiple separate reaction vessels such that each reaction vessel comprises preferably one compartment, or encapsulating said compartment in emulsion droplets such that each droplet comprises preferably one compartment; linking said at least two target nucleic acid molecules.

DEFINITIONS

Herein, a "sample" is a sample of bodily fluid, e.g. from a patient which is to be subjected to the herein disclosed method, for example to be diagnosed. Such samples may be from a human, a plant or an animal. Preferred samples include blood, serum, plasma, cerebrospinal fluid, urine, saliva, sputum, and pleural effusions. In addition, one of skill in the art would realize that some test samples would be more readily analyzed following a fractionation or purification procedure, for example, separation of whole blood into serum or plasma components.

Thus, in a preferred embodiment of the invention the sample is selected from the group comprising a blood sample, a serum sample, a plasma sample, a cerebrospinal fluid sample, a saliva sample and a urine sample or an extract of any of the aforementioned samples. Preferably, the sample is a blood sample, most preferably a serum sample or a plasma sample. In a specific embodiment, the sample includes tissue, a cell, a bacterium and/or a virus.

Herein "tissue" is a cellular organizational level intermediate between cells and a complete organism. A tissue is an ensemble of cells, not necessarily identical, but from the same origin, that together carry out a specific function (blood, liver etc.).

Herein a "fraction thereof" or a "fraction from a sample" is any part of the sample such as a part of the tissue, a part of the cell(s), a part of the bacteria and/or viruses that can be isolated in a reproducible manner and has been enriched for a specified subject manner with the tissue, cell(s), bacteria and/or viruses. Typical examples are exosomes, a cellular structure, a sub-cellular compartment, and/or organelle fractions.

Herein "emulsions" are thermodynamically stable, isotropic liquid mixtures of oil, water and surfactant, frequently in combination with a cosurfactant. The aqueous phase may contain salt(s) and/or other ingredients, and the "oil" may actually be a complex mixture of different hydrocarbons and olefins. In contrast to ordinary emulsions, microemulsions form upon simple mixing of the components and do not require the high shear conditions generally used in the formation of ordinary emulsions. The three basic types of microemulsions are direct (oil dispersed in water, o/w), reversed (water dispersed in oil, w/o) and bicontinuous. In ternary systems such as microemulsions, where two immiscible phases (water and 'oil') are present with a surfactant, the surfactant molecules may form a monolayer at the interface between the oil and water, with the hydrophobic tails of the surfactant molecules dissolved in the oil phase and the hydrophilic head groups in the aqueous phase. In a preferred embodiment, the emulsion is a water in oil emulsion.

DETAILED DESCRIPTION OF THE INVENTION

The invention relates to a method for linking at least two target nucleic acid molecules from a single biological compartment, comprising the steps of isolating a fraction from a sample, wherein the fraction comprises the compartment comprising at least two nucleic acid molecules; diluting said fraction and aliquoting the dilution in multiple separate reaction vessels such that each reaction vessel comprises preferably one compartment, or encapsulating said compartment in emulsion droplets such that each droplet comprises preferably one compartment; linking said at least two target nucleic acid molecules.

More specifically, the present invention relates to a method for linking at least two target nucleic acid molecules from a single biological compartment, comprising the steps of:
a. isolating a fraction from a sample, wherein the fraction comprises the compartment comprising at least two nucleic acid molecules,
b. optionally treating the fraction with RNA degrading enzymes;
c. diluting said fraction and aliquoting the dilution in multiple separate reaction vessels such that each reaction vessel comprises preferably one compartment, or encapsulating said compartment in emulsion droplets such that each droplet comprises preferably one compartment,
d. linking said at least two target nucleic acid molecules.

The dilution factor depends on the initial concentration of nucleic acid molecules in the fraction and the amount, e.g. volume, to be aliquoted into multiple reaction vessels. If the initial concentration is unknown or only roughly known, a dilution series may be prepared, e.g. in a 96-well plate. The technique to dilute a fraction down to a single compartment can be applied in analogy to a so-called digital PCR. Digital PCR enables to amplify a single DNA template from minimally diluted samples, therefore generating amplicons that are exclusively derived from one template and can be further analysed.

The present invention can be applied in a method for determining the sequences of at least two target nucleic acid molecules located on separate nucleic acid molecules from a single biological compartment. The present invention can be also applied in a method for analyzing the function of a protein encoded by at least two target nucleic acid sequences located on separate nucleic acid molecules, from a single biological compartment. The present invention can be further applied in a method for in vitro translation of at least two target nucleic acid sequences located on separate nucleic acid molecules, from a single biological compartment.

Accordingly, in a specific embodiment the method further comprises the step of:
a. determining the nucleic acid sequence of at least a portion of said linked target nucleic acid molecules or
b. rearranging and/or subcloning said linked target nucleic acid molecules for phenotypic or functional analyses or
c. in vitro translating said linked target nucleic acid molecules.

The present invention has the advantage that, by the analysis of subcellular compartments, less material is needed than in the methods disclosed in prior art. Whereas prior art relies on the separation and sorting of whole cells, the present invention does not involve any cell sorting, resulting in reduced costs and time consumption. Additionally the method results in higher redundancy of generated linked nucleic acids, so that, e.g. in diagnostic applications the result has a higher validity.

In another embodiment the method relates to a method for determining paired variable target nucleic acid sequences located on separate nucleic acid molecules from a single biological compartment, comprising the steps of:
a. isolating a fraction from a sample, wherein the fraction comprises microsomes from the endoplasmic reticulum comprising mRNA in translocon complexes,
b. diluting said fraction and aliquoting the dilution in multiple separate reaction vessels such that each reaction vessel comprises preferably one compartment, or encapsulating the fraction in emulsion droplets such that each droplet comprises preferably one microsomal structure,
c. linking said two variable nucleic acid molecules, and
d. determining the nucleic acid sequence at least a portion of said linked two nucleic acid molecules.

The methods of the present invention make use of a linking step. The linking step may be done by means of a method selected from the group of:
a. nucleic acid amplification,
b. polymerase chain reaction amplification,
c. site-specific recombination,
d. ligation and/or
e. tagging of the target nucleic acid molecules with a nucleic acid barcode sequence.

The linking is preferably done using PCR, but it may also be done with other methods. An amplification step is however preferred, prior to sequencing. Here an overlap extension primer mix is used that binds and links both nucleic acids; see also FIG. 1.

The methods of the present invention preferably comprise amplification of the nucleic acids. The amplification may be performed by a variety of known amplification methods. Hence, in one embodiment of the present invention the amplification is performed by a method selected from the group consisting of polymerase chain reaction (PCR), isothermal amplification (such as in Walker, et al., "Strand displacement amplification—an isothermal, in vitro DNA amplification technique," Nucleic Acids Res. 20(7):1691-6 (1992)), ligase chain reaction (LCR; such as in Landegren, et al., "A Ligase-Mediated Gene Detection Technique," Science 241:1077-1080, 1988, or, in Wiedmann, et al., "Ligase Chain Reaction (LCR)—Overview and Applications," PCR Methods and Applications (Cold Spring Harbor Laboratory Press, Cold Spring Harbor Laboratory, NY, 1994) pp. S51-S64)), transcription-based amplification system (TAS), nucleic acid sequence based amplification (NASBA; Kievits et al. (1991) J Virol Methods 35:273-286) rolling circle amplification (RCA; such as in Liu, et al., "Rolling circle DNA synthesis: Small circular oligonucleotides as efficient templates for DNA polymerases," J. Am. Chem. Soc. 118:1587-1594 (1996)), transcription-mediated amplification (TMA; Vuorinen et al. (1995) J Clin Microbiol 33: 1856-1859), self-sustaining sequence replication (3SR), Q13 amplification, strand displacement amplification (SDA) (Walker et al. (1992) Nucleic Acids Res 20(7):1691-6), multiple displacement amplification (MDA) (Dean et al. (2002) Proc Natl Acad Sci USA 99(8): 5261-5266), restriction aided RCA (Wang et al. (2004) Genome Res 14:2357-2366), single primer isotheinial amplification (SPIA; Dafforn et al. (2004) Biotechniques 37(5):854-7), loop mediated isothermal amplification (LAMP; Notomi et al. (2000) Nucleic Acids Res 28(12):e63), transcription mediated amplification (TMA), helicase-dependent amplification (HDA), thermostable HDA (tHDA) (An et al. (2005) J Biol Chem 280(32):28952-28958), smart-amplification process (SMAP; Mitani et al. (2007) Nat Methods 4(3):257-62)), quantitative real-time PCR (qPCR), or reverse-transcriptase PCR (RT-PCR).

Site-specific recombination is a genetic recombination technique in which DNA strand exchange takes place between segments possessing only a limited degree of sequence homology. Site-specific recombinases perform rearrangements of DNA segments by recognizing and binding to short DNA sequences, at which they cleave the DNA backbone, exchange the two DNA helices involved and rejoin the DNA strands. Recombination sites are typically between 30 and 200 nucleotides in length and consist of two motifs with a partial inverted-repeat symmetry, to which the recombinase binds, and which flank a central crossover sequence at which the recombination takes place. For further particulars we refer the reader to: Kolb, A. F. (2002). "Genome Engineering Using Site-Specific Recombinases". Cloning & Stem Cells 4 (1): 65-80.

While the above techniques aim at a physical linkage of the target nucleic acids, the present method embraces an informational linkage as well. For example, all nucleic acid molecules from the same compartment can be tagged with the same unique nucleic acid barcode sequence. Subsequently, this barcode sequence can be used to infer that the nucleic acid molecules were present in the same compartment. Tagging of nucleic acid molecules with a nucleic acid barcode sequence can be accomplished by PCR using clonal barcode primers immobilized to bead particles or long rolling circle amplification products composed of many barcode repeats.

The determining the nucleic acid sequence step is preferably done by sequencing, more preferably by next generation sequencing. Of particular use are massively parallel next-generation sequencing techniques.

The next generation sequencing technique may be sequencing by synthesis, pyro sequencing, sequencing by oligo ligation, semiconductor technology or single molecule real-time (SMRT™) sequencing. However, the herein disclosed method is not restricted to next generation sequencing methods. For example, Sanger sequencing may be performed as well. Preferably the read lengths of the next generation sequencing method used are as high as possible but that must not be necessary. They may be, e.g., single end 36 or up to 150 bases or 2×36 up to 2×150 bases paired end (ILLUMINA™), single end up to 50 bases or 75 bases paired-end: 75 bp×35 bp (SOLID™), up to 700-800 bases (Roche), or up to 100-200 bases single end or paired end (ION TORRENT™). Illumina 2×150 bases paired end reads or Roche GS FLX+ single end reads up to 1000 bases are preferred.

Specific examples of sequencing techniques are:

(i) ILLUMINA™ (described in: Hillier et al. Nat Methods. 2008 February; 5(2): 183-8): HISEQ™ 2000, HISEQ™ 1000, Genome Analyzer IIx, MISEQ, HiScanSQ (chemistry: Sequencing by synthesis), (ii) Roche: Roche 454 (described in: Binladen et al. PLoS One. 2007 Feb. 14; 2(2):e197) GS FLX, GS FLX+, GS Junior (chemistry: Pyrosequencing), (iii) Invitrogen: SOLiD 5500 Series (described in: loosterman et al. Hum Mol Genet. 201 1 May 15; 20(10): 1916-24) (chemistry: sequencing by oligo ligation), (iv) Invitrogen: ION TORRENT™ PGM (described in: Rothberg et al. Nature. 2011 Jul. 20; 475(7356):348-52) or ION PROTON™ Sequencer (chemistry: semiconductor technology), (v) Pacific Biosciences (described in: Flusberg et al. Nat Methods. 2010 June; 7(6):461-5): PacBio RS system (chemistry: single molecule, real-time (SMRT™) sequencing).

The rearranging and/or subcloning step is preferably done by a method selected from the group of assembly by overlap extension polymerase chain reaction, site-specific recombination, and/or ligation.

Phenotyping or functional analysis in the context of the present invention means analysis of the protein encoded by the linked at least two nucleic acids with respect to its function. The function of a protein can be assessed in terms of bioactivity, enzymatic activity, binding efficiency using an assay such as an ELISA, surface plasmon resonance (SPR, Biacore), binding assays on protein microarrays, or other bioassays, Rearranging nucleic acid molecules in the context of the present invention means bringing the two or more nucleic acid sequences of interest into an arrangement that, together with other flanking nucleic acid sequences, allows for expression of functional proteins, for example single-chain variable fragment (scFv) antibodies where the variable regions of the heavy (VH) and light chains (VL) of immunoglobulins are connected with a short linker peptide.

Subcloning is a technique used to move a particular gene of interest from a parent vector to a destination vector in order to further study its functionality. Restriction enzymes are used to excise the gene of interest (the insert) from the parent. The insert is purified, e.g. by gel isolation, and the gene of interest is then amplified using for example Polymerase Chain Reaction (PCR). Simultaneously, the same restriction enzymes are used to digest (cut) the destination such that complementary sticky ends are created, which will facilitate ligation later on. A phosphatase (commonly Calf Intestinal Alkaline Phosphatase; CIAP) is usually added to prevent self-ligation of the destination vector. The digested destination vector is then isolated and/or purified. The insert and the destination vector are then mixed together with DNA ligase. A typical ratio of insert genes to destination vectors is 3:1; by increasing the insert concentration, self-ligation is further decreased. Upon incubation at a specific temperature (dependent upon the size of the strands being ligated), the insert should become successfully incorporated into the destination plasmid. The plasmid is often transformed into a bacterium, such as *E. coli*. After a good number of bacterial colonies have grown, they can be miniprepped to harvest the plasmid DNA. For selection of the transformed bacteria (which carry the desired plasmids to be harvested), a marker gene (e.g. antibiotic resistance or nutrient biosynthesis) is incorporated into the plasmid which enables the successfully transformed bacteria only to grow in the selective media (e.g. ampicillin).

For in vitro translation, the most frequently used cell-free translation systems consist of extracts from rabbit reticulocytes, wheat germ and *Escherichia coli*. All are prepared as crude extracts containing all the macromolecular components (70S or 80S ribosomes, tRNAs, aminoacyl-tRNA synthetases, initiation, elongation and termination factors, etc.) required for translation of exogenous RNA. To ensure efficient translation, each extract must be supplemented with amino acids, energy sources (ATP, GTP), energy regenerating systems (creatine phosphate and creatine phosphokinase for eukaryotic systems, and phosphoenol pyruvate and pyruvate kinase for the *E. coli* lysate), and other co-factors (Mg2+, K+, etc.). There are two approaches to in vitro protein synthesis based on the starting genetic material: RNA or DNA. Standard translation systems, such as reticulocyte lysates and wheat germ extracts, use RNA as a template; whereas "coupled" and "linked" systems start with DNA templates, which are transcribed into RNA then translated. For example, Ambion offers a nuclease-treated reticulocyte lysate. This type of lysate is the most widely used RNA-dependent cell-free system because of its low background and its efficient utilization of exogenous RNAs even at low concentrations. Exogenous proteins are synthesized at a rate close to that observed in intact reticulocyte cells.

The in vitro translating step used in the herein disclosed method is not restricted to a particular method; however, it is preferably done by cell-free in vitro translation. Therefore, coupled or uncoupled transcription and translation kit can be used. The cell-free translation kit may be of prokaryotic or eukaryotic origin. The resulting protein may be secreted into microsomes or anchored to a surface using tag or domain fusions for functional display or detection.

In the context of the present invention the target nucleic acid molecules may be, inter cilia, RNA, DNA, cDNA (complementary DNA), mRNA (messenger RNA), mtRNA (mitochondrial RNA), rRNA (ribosomal RNA), tRNA (transfer RNA), nRNA (nuclear RNA), siRNA (short interfering RNA), snRNA (small nuclear RNA), snoRNA (small nucleolar RNA), scaRNA (Small Cajal Body specific RNA), microRNA, dsRNA (doubled-stranded RNA), ribozyme, riboswitch, viral RNA, dsDNA (double-stranded DNA), ssDNA (single-stranded DNA), plasmid DNA, cosmid DNA, chromosomal DNA, viral DNA, mtDNA (mitochondrial DNA), nDNA (nuclear DNA) and snDNA (small nuclear DNA). Preferably however, the target nucleic acids are cDNA (complementary DNA), mRNA (messenger RNA), mtRNA (mitochondrial RNA), nRNA (nuclear RNA), microRNA, dsRNA (doubled-stranded RNA), viral RNA, dsDNA (double-stranded DNA), ssDNA (single-stranded DNA), plasmid DNA, chromosomal DNA, viral DNA, mtDNA (mitochondrial DNA), nDNA (nuclear DNA). More preferably, the target nucleic acid molecules are mRNA.

It is preferred that the target sequences are selected from the group of cell-specific single nucleotide polymorphisms, cell-specific variable sequence regions, cell-specific splice variants, sequences encoding VH (variable heavy chain) domains and VL (variable light chain) domains and sequences encoding T cell receptor alpha and beta chains. Herein, also portions of the regions may be meant. For example not the entire VH or VL must be analyzed. In a preferred embodiment both VH and VL are the target sequences.

A single nucleotide polymorphism (SNP) is a DNA sequence variation occurring when a single nucleotide—A, T, C or G—in the genome (or other shared sequence) differs between members of a biological species or paired chromosomes in an individual. For example, two sequenced DNA fragments from different individuals, AAGCCTA to AAGCTTA, contain a difference in a single nucleotide. SNPs can occur in both coding and non-coding regions of genome.

There are five types of mammalian Ig heavy chain denoted by the Greek letters: α, δ, ε, γ, and μ. The type of heavy chain present defines the class of antibody; these chains are found in IgA, IgD, IgE, IgG, and IgM antibodies, respectively. Distinct heavy chains differ in size and composition; α and γ contain approximately 450 amino acids, while g and E have approximately 550 amino acids. Each heavy chain has two regions, the constant region and the variable region. The constant region is identical in all antibodies of the same isotype, but differs in antibodies of different isotypes. Heavy chains γ, α and δ have a constant region composed of three tandem (in a line) Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain. In mammals there are two types of immunoglobulin light chain, which are called lambda (λ) and kappa (κ). A light chain has two successive domains: one constant domain and one variable domain. The approximate length of a light chain is 211 to 217 amino acids. Each antibody contains two light chains that are always identical; only one type of light chain, κ or λ, is present per antibody in mammals.

The T-cell receptor (TCR), which is anchored in the cell membrane, consists of two halves, which form a pair (or dimer) of protein chains. The halves are called the alpha (α) and beta (β) fragments (in γ/δ T cells, the halves are gamma (γ) and delta (δ) fragments). Each fragment is divided in turn into a constant (C) and variable (V) region. The constant region has an end that is anchored in the cell membrane. The variable region faces outward and binds to the HLA molecule and the antigen it presents. On the α chain, the variable region is called Vα and the constant region is called Cα; on the β chain, they are called Vβ and Cβ, respectively.

In another embodiment of the method for linking at least two target nucleic acid molecules the target nucleic acid molecules encode for a single-chain variable fragment (scFv). A scFv is a fusion protein of the variable regions of the heavy (VH) and light chains (VL) of immunoglobulins, connected with a short linker peptide of ten to about 25 amino acids. The linker is usually rich in glycine for flexibility, as well as serine or threonine for solubility, and can either connect the N-terminus of the VH with the C-terminus of the VL, or vice versa. This protein retains the specificity of the original immunoglobulin, despite removal of the constant regions and the introduction of the linker. These molecules were created to facilitate phage display, where it is highly convenient to express the antigen-binding domain as a single peptide. As an alternative, scFv can be created directly from subcloned heavy and light chains derived from a hybridoma. ScFvs have many uses, e.g., flow cytometry, immunohistochemistry, and as antigen-binding domains of artificial T cell receptors. Unlike monoclonal antibodies, which are often produced in mammalian cell cultures, scFvs are more often produced in bacteria cell cultures such as E. coli.

The herein disclosed methods find its use in a variety of applications where different nucleic acid variants act together in biological compartments, such as cells, to determine the specific biological behavior. For example, this technique offers the possibility to determine if two or more mutations are present in a single cell. This is particular useful in cases where two mutations in two different signaling pathway molecules can result in malignancy of individual cancer cells, whereas other cells in the same tumor population that carry only one of these mutations are non-malignant. Furthermore, the associated T cell receptor alpha and beta chain genes, as well as the nucleic acid sequences encoding VH (variable heavy chain) domains and VL (variable light chain) domains of a single antibody can be easily determined.

In summary, the present invention may be used in one of the following applications:
- pre-selecting or characterizing hybridoma cells
- determining immune repertoires from blood samples by sequencing the paired VH and VL repertoire from B cells and/or the paired T cell receptor alpha and beta chain repertoire from T cells
- monitoring changes in the immune repertoire accompanying vaccination, infection, autoimmune disorders and other circumstances affecting the immune system
- diagnosing blood or urine on the presence of mutations (e.g. cancer diagnosis from exosomal RNA)
- determining mutations in bacteria arising from treatment with antibiotics
- determining mutations in viruses arising from treatment with antiviral drugs
- determining associated nucleic acid sequences encoding for a fusion protein
- in vitro translation of fusion proteins, antibodies and antibody fragments including scFv fragments A (biological) compartment herein relates preferably to a morphologically and/or spatially segregated part of a cell. As such it comprises a single cell, a sub-cellular compartment, an exosome, a bacterium or a viral particle.

A sub-cellular compartment means all of the closed parts within the cytosol of a eukaryotic cell, usually surrounded by a single or double lipid layer membrane. Most organelles are compartments: mitochondria, chloroplasts (in photosynthetic organisms), peroxisomes, lysosomes, the endoplasmic reticulum, the cell nucleus or the Golgi apparatus. Smaller elements like vesicles, and even microtubules may also be counted as compartments.

Exosomes are 30-90 nm vesicles secreted by a wide range of mammalian cell types. Exosomes can be concentrated and separated from other components in a sample by differential centrifugation.

In one embodiment the compartment is morphologically and/or spatially segregated by a membrane. This means that the target nucleic acid molecules are enclosed in a membrane or associated with a membrane. Accordingly, a membrane herein is not restricted to an enclosing membrane, but rather includes incomplete membranes and membrane fractions. Preferably, such compartment is selected from the group of microsomes, stress granules, plasmodesmata, mitochondria, chloroplasts, chromoplasts, leukoplasts and apicoplasts.

In other embodiments, the compartment does not comprise a membrane. In this case, the target nucleic acids are not enclosed in a membrane or associated with a membrane. In this embodiment, the compartment is preferably selected from the group of cellular nucleoli, P bodies, centrioles.

Microsomes are vesicle-like artifacts re-formed from pieces of the endoplasmic reticulum (ER) when eukaryotic cells are broken-up in the laboratory. Microsomes are not ordinarily present in living cells. Microsomes can be concentrated and separated from other cellular debris by differential centrifugation. Unbroken cells, nuclei, and mitochondria sediment out at 10,000 g, whereas soluble enzymes and fragmented ER, which contains cytochrome P450 (CYP), remain in solution. At 100,000 g, achieved by faster centrifuge rotation, ER sediments out of solution as a pellet but the soluble enzymes remain in the supernatant. In this way, cytochrome P450 in microsomes is concentrated and isolated. In one embodiment the microsomes are derived from the endoplasmatic reticulum (ER). Preferably these contain mRNA sequences in translocon complexes. The translocon is the complex of proteins associated with the translocation of nascent polypeptides across membranes. In eukaryotes the polypeptides are transported into the interior (cisternal or luminal) space of the endoplasmic reticulum (ER) from the cytosol.

Stress granules are dense aggregations in the cytosol composed of proteins & RNAs that appear when the cell is under stress. The RNA molecules stored are stalled translation pre-initiation complexes—failed attempts to make protein from mRNA. Stress granules are 100-200 nm in size, not surrounded by membrane, and associated with the endoplasmatic reticulum.

The compartment may also be a nucleus. In this case the use of specific recombinases may help to cope with the rather high concentration of DNA within the nucleus which would lead to a high background. A nucleus is a membrane-enclosed organelle found in eukaryotic cells. It contains most of the cell's genetic material, organized as multiple long linear DNA molecules in complex with a large variety of proteins, such as histones, to form chromosomes.

Plasmodesmata (singular: plasmodesma) are microscopic channels which traverse the cell walls of plant cells and some algal cells, enabling transport and communication between them. Species that have plasmodesmata include members of the Charophyceae, Charales and Coleochaetales (which are all algae), as well as all embryophytes, better known as land plants. Unlike animal cells, every plant cell is surrounded by a polysaccharide cell wall. Neighbouring plant cells are therefore separated by a pair of cell walls and the intervening lamella, forming an extracellular domain known as the apoplast. Although cell walls are permeable to small soluble proteins and other solutes, plasmodesmata enable direct, regulated, symplastic intercellular transport of substances between cells. There are two forms of plasmodesmata: primary plasmodesmata, which are formed during cell division, and secondary plasmodesmata, which can form between mature cells.

A mitochondrion (plural mitochondria) is a membrane-enclosed organelle found in most eukaryotic cells. These organelles range from 0.5 to 1.0 micrometer (μm) in diameter. Mitochondria are sometimes described as "cellular power plants" because they generate most of the cell's supply of adenosine triphosphate (ATP), used as a source of chemical energy. In addition to supplying cellular energy, mitochondria are involved in a range of other processes, such as signaling, cellular differentiation, cell death, as well as the control of the cell cycle and cell growth. Special means for isolating mitochondria have been created for various tissues and plants and other organisms, even kits exist (www.mitosciences.com/PDF/mitos.pdf).

Chloroplasts are organelles found in plant cells and other eukaryotic organisms that conduct photosynthesis. Chloroplasts capture light energy to conserve free energy in the form of ATP and reduce NADP to NADPH through a complex set of processes called photosynthesis.

Chromoplasts are plastids responsible for pigment synthesis and storage. They, like all other plastids (including chloroplasts and leucoplasts), are organelles found in specific photosynthetic eukaryotic species. Chromoplasts synthesize and store pigments such as orange carotene, yellow xanthophylls, and various other red pigments; as such, their color varies depending on what pigment they contain. They allow the accumulation of large quantities of water-insoluble compounds in otherwise watery parts of plants. In chloroplasts, some carotenoids are also used as accessory pigments in photosynthesis, where they act to increase the efficiency of chlorophyll in harvesting light energy.

Leucoplasts are a category of plastid and as such are organelles found in plant cells. They are non-pigmented, in contrast to other plastids such as the chloroplast. Lacking pigments, leucoplasts are not green. They are white and colorless, so they are predictably located in roots and non-photosynthetic tissues of plants. They may become specialized for bulk storage of starch, lipid or protein and are then known as amyloplasts, elaioplasts, or proteinoplasts respectively. However, in many cell types, leucoplasts do not have a major storage function and are present to provide a wide range of essential biosynthetic functions, including the synthesis of fatty acids, many amino acids, and tetrapyrrole compounds such as haem.

An apicoplast is a derived non-photosynthetic plastid found in most Apicomplexa, including malaria parasites such as *Plasmodium falciparum*, but not in others such as *Cryptosporidium*. It originated from an algae through secondary endosymbiosis. The apicoplast is surrounded by four membranes within the outermost part of the endomembrane system.

The nucleolus (plural nucleoli) is a non-membrane bound structure composed of proteins and nucleic acids found within the nucleus. Ribosomal RNA (rRNA) is transcribed and assembled within the nucleolus. Three major components of the nucleolus are recognized: the fibrillar centers (FC), the dense fibrillar components (DFC), and granular components (GC). The DFC or pars fibrosa consists of newly transcribed rRNA bound to ribosomal proteins, while the GC, called pars granulosa, contains rRNA bound to ribosomal proteins that are beginning to assemble into ribosomes. However, it has been proposed that this particular organization is only observed in higher eukaryotes and that it evolved from a bipartite organization with the transition from anamniotes to amniotes. Reflecting the substantial increase in the DNA intergenic region, an original fibrillar component would have separated into the FC and the DFC. Another structure identified within many nucleoli (particularly in plants) is a clear area in the center of the structure referred to as a nucleolar vacuole.

P-bodies are distinct foci within the cytoplasm of the eukaryotic cell consisting of many enzymes involved in mRNA turnover. P-bodies have been observed in somatic cells originating from vertebrates and invertebrates, including plants and yeast. To date, P-bodies have been demonstrated to play fundamental roles in general mRNA decay, nonsense-mediated mRNA decay, AU-rich element mediated mRNA decay, and microRNA induced mRNA silencing. Not all mRNAs which enter P-bodies are degraded, as it has been demonstrated that some mRNAs can exit P-bodies and re-initiate translation. The following activities have been demonstrated to occur in or to be associated with P-bodies: (i) decapping and degradation of unwanted mRNAs, (ii) storing mRNA until needed for translation, (iii) and aiding in translational repression by miRNAs (related to siRNAs).

Centrioles are involved in the organization of the mitotic spindle and in the completion of cytokinesis. Centrioles were previously thought to be required for the formation of a mitotic spindle in animal cells. However, more recent experiments have demonstrated that cells whose centrioles have been removed via laser ablation can still progress through the G1 stage of interphase before centrioles can be synthesized later in a de novo fashion. Centrioles are a very important part of centrosomes, which are involved in organizing microtubules in the cytoplasm. The position of the centrioles determines the position of the nucleus and plays a crucial role in the spatial arrangement of the cell.

In a preferred embodiment of the invention the compartment is the endoplasmatic reticulum, target nucleic acids encode VL and/or VH domains and the linking is performed using primers comprising any of SEQ ID NOs 1-42.

The invention further relates to a kit for performing a method according to the invention, wherein the kit comprises a. an oil and/or one or several detergents for emulsion formation and/or
b. reagents for nucleic acid reverse transcription and/or
c. reagents for nucleic acid amplification.

In a preferred embodiment, the oil is a mineral oil or an silicone oil or a mixture thereof and/or the detergent is selected from the group of sorbitan oleate, polyoxyethylene (20) sorbitan monooleate and polyethylene glycol p-(1,1,3, 3-tetramethylbutyl)-phenyl ether.

In a first specific embodiment the kit further comprises reagents for nucleic acid sequencing. In a second specific embodiment the kit further comprises reagents for in vitro translation. In a third specific embodiment the kit further comprises reagents for nucleic acid rearrangement and/or subcloning for phenotypic or functional analyses.

Reagents for nucleic acid reverse transcription are:

Reagents for nucleic acid amplification are: normal PCR kit, Biomerieux NUCLISENS™ Basic Q, Twis Dx RPA, Biohelix ISOAMP™ kit Reagents for nucleic acid sequencing are those which are commonly used in one of the sequencing methods cited above.

Reagents for in vitro translation are: Qiagen EASYXPRESS™, 5 PRIME RTS, Ambion RETIC LYSATE IVT™, Invitrogen EXPRESSWAY™, NEB PURExpress, Promega TNT®

Reagents for nucleic acid rearrangement and/or subcloning are: Agilent STRATACLONE™ PCR Cloning Kit, Invitrogen GATEWAY™, Cre-loxP, Flp/FRT In a specific embodiment endoplasmic reticulum (ER) microsomes with associated mRNAs, for example from mouse NIH/3T3 cells (ATCC #CRL-1658) and human HEK 293T cells (ATCC #CRL-11268), are used in the herein disclosed method. The mRNA of the ER may be isolated using common techniques. The mRNA may be reverse transcribed and human HSPA5 and HSP90B1 transcript fragments (from HEK 293T microsomes) or mouse Hspa5 and Hsp90b1 transcript fragments (from NIH/3T3 microsomes) in conventional open RT-PCR assembled. The assembly products may be separated on an agarose gel to visualize the obtained products or subjected to alternative analysis methods. By using this embodiment combinations of transcript fragments can be assembled and amplified in a cell type-specific way using the RT-PCR assembly set-up described herein.

In a further specific embodiment clonally paired amplification of human and mouse transcript fragments from mixed human and mouse ER microsomes in emulsion RT-PCR is carried out. In this aspect, an emulsion comprising for example Span 80, Tween 80 and/or TRITON™ X-100 in mineral oil is set up and emulsion RT-PCR is performed. I necessary, the DNA can be purified afterwards. The assembly products may be separated on an agarose gel and the band of interest excised for subsequent analysis, e.g. by secondary PCR amplification using four different mixes of nested primers representing the four possible combinations of the two assembled transcript fragments from human and mouse ER microsomes, namely human-human, human-mouse, mouse-human and mouse-mouse combination of the two genes. The nested PCR products may be run on an agarose gel to visualize the pairing combinations obtained from the RT-PCR assembly reactions. By applying this embodiment emulsion RT-PCR assembly from ER microsome transcripts results in strong enrichment of clonal pairings of endogenous transcript variants, representing the endogenous transcript pairing in the original cells.

In another specific embodiment endoplasmic reticulum (ER) microsomes with associated mRNAs from different hybridoma cells may be used in the herein disclosed method. The mRNA of the ER may be isolated using common techniques. As a control experiment, the immunoglobulin VL and VH sequences from ER microsomes of each hybridoma cell line may be amplified, reverse transcribed and linked separately. Primer sequences for specific amplification of mouse IgM heavy chain VH sequences and kappa light chain VL sequences may be based on primers described before (Wang et al. 2000). The assembly products from the open RT-PCR may be run on an agarose gel. After excision of agarose gel slices with the DNA of interest, the DNA may be purified. The assembled VL+VH sequences may be used as templates for PCR to further amplify each separate VL and VH sequence and each VL+VH assembly which may be visualized by agarose gel electrophoresis or determined by sequencing, e.g. Sanger sequencing. By using this embodiment, the endogenous VL and VH pairing in antibody-producing cells may be assembled and analyzed.

Clonally paired amplification of immunoglobulin VH and VL sequences from mixed hybridoma ER microsomes in emulsion RT-PCR may be further applied as described above to enrich clonal pairings of endogenous transcript variants, representing the endogenous transcript pairing in the antibody-producing hybridoma cells.

The invention further relates to a method for the determination of the immune status of an organism, comprising the steps of:

(a) Obtaining a sample from said organism comprising subcellular compartments of cells of said organisms, (b) diluting said sample and with a method according to claim one, linking the nucleic acid sequences in the sample together; (c) determining the nucleic acid sequence of nucleic acids relating to VH and VL sequences from said sample.

Another embodiment of the invention relates to a method for the production of monoclonal antibodies or antibody variants comprising the steps of (a) The use of the disclosed methods to generate a linked nucleic acid comprising the nucleic acid sequence of VH and/or VL domain of an antibody or fragment thereof; (b) analyzing the nucleic acid sequence of the linked nucleic acids to determine the nucleic acid sequences of the VH and/or VL domain or fragment thereof; (c) generation of at least one expression vector comprising the determined sequence of the VH and/or the VL domain or fragment thereof, wherein the determined sequence is optionally attached to a sequence corresponding to the constant region of an antibody or wherein the VL and/or VH domain are linked to form an antibody fragment; (d) heterologous expression of the expression vector in a suitable host cell and subsequent purification of the recombinant antibody or antibody fragment.

In a preferred embodiment the constant region of an antibody or antibody variant to which the determined sequence is attached is selected from the group comprising IgG, IgA, IgD, IgM and IgE.

In another preferred embodiment of the invention the VL and/or VH domain are linked to form an antibody fragment selected from the group comprising: Fab-fragment, F(ab)$_2$ fragment, variable fragment (Fv), single chain Fv, disulphide linked Fv and single chain Fv dimer.

The Invention further relates to an antibody produced by a method as described above.

A. A genetically heterogenous cell population was created by mixing (1:1) human HEK 293T cells and mouse NIH/3T3 cells. B. ER microsomes with associated mRNAs in translocon complexes were isolated from cycloheximide-treated cells. C. The ER microsomes, each associated with ribosomes and mRNAs from one single cells, were suspended in a RT-PCR mix containing the suitable primers for reverse transcription and assembly of two ER-associated mRNAs. The RT-PCR mix with microsomes was emulsified in a mineral oil phase with detergents, such that each droplet contained preferentially zero or one microsome from one single cell. D. Two outer primers (O1 and O2) were used for reverse transcription and further amplification of the assembled DNA sequences, while two inner primers (I1 and I2) with common overlap sequences were used to assemble the two different mRNAs during using PCR assembly. E. Each assembly product contained DNA sequences derived from the two different mRNAs from one single cell, linked together by an inner linker sequence and flanked by two universal outer adapter sequences used for further amplification. F. The resulting assembled DNA sequences were analyzed for the origin of the two RNA sequences (human or mouse) using four different nested primers, namely N1(human), N1(mouse), N2(human) and N2(mouse) to determine the pairing combinations and to verify the preferential pairing of human RNA1 with human RNA2 and of mouse RNA1 with mouse RNA2.

FIGS. 2A-2B: Products obtained from RT-PCR assembly using human or mouse ER microsomes.

A. RT-PCR assembly products obtained using human microsomes from HEK 293T cells. Lane 4—the use of human-specific assembly primer mix results in the assembly of human HSPA5 and human HSP90B1 transcript fragments, visible at 223 bp, while the separate products from HSP90B1 alone (108 bp) and HSPA5 alone (142 bp) are less prominent. Lane 3—replacement of human outer primer O2 by mouse outer primer O2 prevents amplification of human HSP90B1, resulting in the amplification of human HSPA5 alone. Lane 2—replacement of human outer primer O1 by mouse outer primer O1 prevents amplification of human HSPA5, resulting in the amplification of human HSP90B1 alone. Lane 1—negative control without ER microsomes. B. RT-PCR assembly products obtained using mouse ER microsomes from NIH/3T3 cells. Lane 4—the use of mouse-specific assembly primer mix results in the assembly of mouse Hspa5 and mouse Hsp90b1 transcript fragments, visible at 223 bp, while the separate products from Hsp90b1 alone (108 bp) and Hspa5 alone (142 bp) are less prominent. Lane 3—replacement of mouse outer primer O2 by human outer primer O2 prevents amplification of mouse Hsp90b1, resulting in the amplification of mouse Hspa5 alone. Lane 2—replacement of mouse outer primer O1 by human outer primer O1 prevents amplification of mouse Hspa5, resulting in the amplification of mouse Hsp90b1 alone. Lane 1—negative control without ER microsomes.

Figure 3:
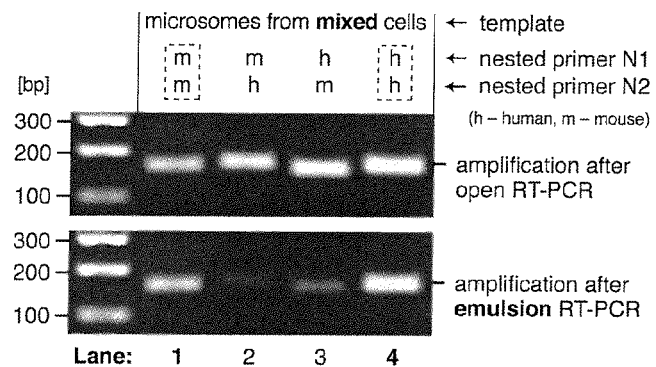

FIG. 3: Products obtained from semi-quantitative PCR using assemblies from mixed human and mouse ER microsomes as template.

Upper panel—The assemblies obtained by open RT-PCR from mixed ER microsomes consist of all four possible combinations between the two mouse genes and the two human genes, with the artifical combinations mouse-human (lane 2) and human-mouse (lane 3) representing a large fraction of the total assemblies. Lower panel—The assemblies obtained by emulsion RT-PCR from mixed ER microsomes are strongly enriched in the native combinations mouse-mouse (lane 1) and human-human (lane 4), representing the endogenous transcript pairing present in the original cells.

Figure 4:
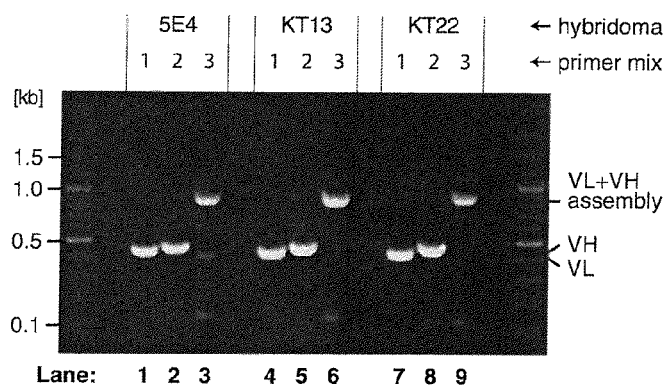

FIG. 4: VL and VH chains and the assembly products after RT-PCR assembly from ER microsomes of 5E4, KT13 and KT22 hybridoma cells.

Three different combinations of outer adapter primers and inner linker primers were used to amplify the separate VL and VH chains and the assembly products after RT-PCR assembly from ER microsomes of 5E4, KT13 and KT22 hybridoma cells. Lanes 1, 4 and 7—Amplification product of the immunoglobulin VL sequence from 5E4, KT13 and KT22 hybridoma cells, respectively. Lanes 2, 5 and 8—Amplification product of the immunoglobulin VH sequence from 5E4, KT13 and KT22 hybridoma cells, respectively. Lanes 3, 6 and 9—Amplification product of the assembled immunoglobulin VL+VH sequences from 5E4, KT13 and KT22 hybridoma cells, respectively.

Figure 5:
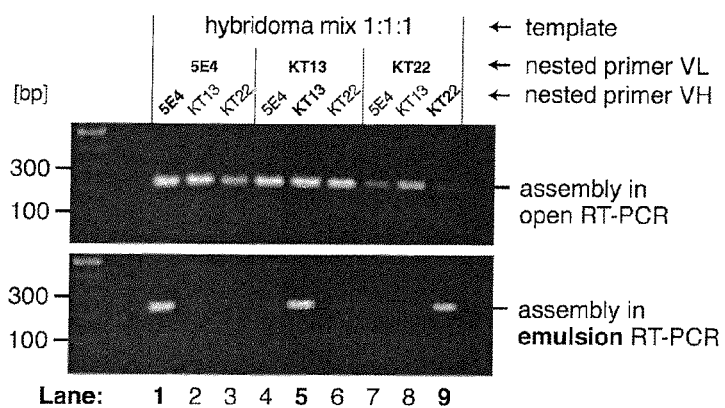

FIG. 5: Products obtained from semi-quantitative PCR using assemblies from mixed hybridoma ER microsomes as template.

Upper panel—The assemblies obtained by open RT-PCR from mixed ER microsomes consist of all nine possible combinations between the three immunoglobulin VL and VH sequences, of which six are artificial combinations not present in the original hybridoma cells. Lower panel—The assemblies obtained by emulsion RT-PCR from mixed ER microsomes are strongly enriched in the native combinations 5E4 VL+VH (lane 1), KT13 VL+VH (lane 5) and KT22 VL+VH (lane 9), representing the endogenous transcript pairing present in the original hybridoma cells.

Figure 6:
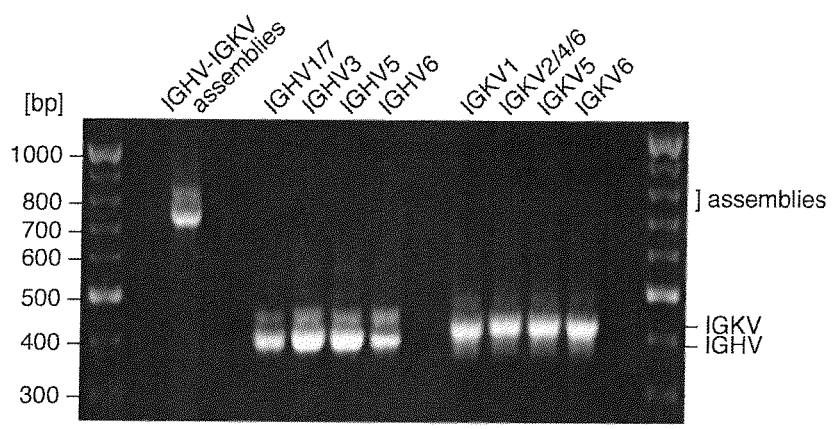

FIG. 6: Agarose gel picture showing a complex mixture of assembled human immunoglobulin heavy and light chains.

The lane "IGHV-IGKV assemblies" shows DNA assemblies obtained from RT-PCR assembly of a complex mixture of human immunoglobulin heavy and light chain sequences, further amplified by emulsion PCR. The other lanes show that these assemblies contain heavy chains and light chains from several different immunoglobulin gene families, as detected by analytical PCR with the family-specific primers listed in Table 7. The lanes "IGHV1/7", "IGHV5" and "IGHV6" show PCR products, using the assemblies as template, obtained with forward primers for the respective variable heavy chain families (I1_hj_VH17_Briney, I1_hj_VH3_Briney, I1_hj_VH5_Briney, or I1_hj_VH6_Briney) and reverse IgM constant region primer (O1_MID1_IgMc_Wang). The lanes "IGKV1", "IGKV2/4/6", "IGKV3" and "IGKV5" show PCR products, using the assemblies as template, obtained with forward primers for the respective variable kappa light chain families (I2_jh_VK1_Lim, I2_jh_VK246_Lim, I2_jh_VK3_Lim, or I2_jh_VK5_Lim) and reverse Ig kappa constant region primer (O2_MID12_IgKc_Wang).

EXAMPLES

Example 1

Determination of Combinations of Single-Nucleotide Polymorphisms (SNPs) on the Level of Single Cells Mouse NIH/3T3 cells (ATCC #CRL-1658) and human HEK 293T cells (ATCC #CRL-11268) were obtained from the American Type Culture Collection. Adherent cells in 150 cm2 bottles were grown at 15-80% confluence in DMEM medium (with 4.5 g/l glucose, Gibco #41966-052) with 10% FBS (Biochrom #S0615) and 1× Penicillin/Streptomycin (Gibco #15140-122) at 37° C. in 5% CO2 and 92% relative humidity. Cycloheximide-treated frozen cell pellets were prepared from 70-80% confluent cells as follows. Cycloheximide was added to the medium to 0.1 mg/ml final concentration, and the cells were incubated for 10 min at 37° C. The medium was removed and the cells were washed with 10 ml cold PBS. After removal of the PBS, 2 ml Trypsin solution with 0.05 mg/ml cycloheximide were added, and the cells were incubated at room temperature until the cell layer was dispersed (0.5-1 min for HEK cells, 5-15 min for 3T3 cells). After addition of 8 ml DMEM, the cells were transferred into a 50 ml Falcon tube and kept on ice until centrifugation. Cells were pelleted by centrifugation with 600 g for 5 min at 4° C. and resuspended in cold PBS with 0.05 mg/ml cycloheximide at a concentration of 1 million cells per ml. The suspension was aliquoted a 1 ml in new 1.5 ml centrifuge tubes. After centrifugation with 600 g for 5 min at 4° C., the supernatant was removed, the cell pellets were snap-frozen in liquid nitrogen and stored at −80° C. until use. Mixed cells pellets were prepared by mixing together equal amounts of HEK 293T and NIH/3T3 cells after trypsinization and before centrifugation.

For preparation of endoplasmic reticulum (ER) microsomes with associated mRNAs, frozen cell pellets of 1 million cells were resuspended in 120 µl cold MP HD buffer (25 mM HEPES-KOH pH 7.2, 110 mM KOAc, 5 mM Mg(OAc)2, 1 mM EGTA, 25% (w/w) sucrose, 5% (v/v) glycerol, 1 mM DTT, 1× Complete EDTA-free proteinase inhibitor cocktail, 0.1 mg/ml cycloheximide, 0.015% digitonin and 80 U/ml RNase Inhibitor [Ambion]). The suspension was pipetted up and down for 15 times to lyze the cells and incubated on ice for 5 min. The homogenate was split à 55 μl into fresh 1.5 ml centrifuge tubes and centrifuged with 600 g for 3 min at 4° C. to pellet nuclei and debris. The supernatants containing membranes and cytosol were transferred à 40 μl into fresh 1.5 ml centrifuge tubes, and the sucrose was diluted to 12-13% (w/w) by addition of 40 μl nuclease-free water to each tube. After mixing by pipetting 5 times up and down and 10 times tapping the tubes, ER microsomes were pelleted by centrifugation with 20,800 g for 90 min at 4° C. in an Eppendorf centrifuge 5810 R (rotor F-45-30-11). The supernatant (cytosol) was transferred into a fresh 1.5 ml tube on ice, frozen on dry ice and stored at −80° C. until use. The ER microsome pellets were resuspended in 90 μl Wash buffer (25 mM HEPES-KOH pH 7.2, 110 mM KOAc, 2.5 mM Mg(OAc)2, 1 mM EGTA, 1 mM DTT, 1× Complete EDTA-free proteinase inhibitor cocktail, 0.1 mg/ml cycloheximide, 0.004% digitonin and 80 U/ml RNase Inhibitor [Ambion]) by pipetting 10 times up and down. The ER microsomes were pelleted by centrifugation with 20,800 g for 45 min at 4° C. After removal of the supernatants, the ER microsome pellets were snap-frozen in liquid N2 and store at −80° C. until use.

For reverse transcription and assembly of human HSPA5 and HSP90B1 transcript fragments (from HEK 293T microsomes) or mouse Hspa5 and Hsp90b1 transcript fragments (from NIH/3T3 microsomes) in conventional open RT-PCR, each ER microsome pellet was resuspended in 20 pal Wash buffer by pipetting 10 times up and down. Reverse transcription and assembly was carried out in 50 μl reactions containing 1× Verso 1-Step PCR Master Mix (Thermo Scientific), 0.5 μg/μl BSA, 1× Verso Enzyme Mix (Thermo Scientific), 4 μl of the appropriate primer mix and 4 μl human microsomes or 4 μl mouse microsomes. Primer sequences are listed in Table 1.

For assembly of human HSPA5 and HSP90B1 transcript fragments, the primer mix contained 5 μM TitA_hHSPA5_O1, 1 μM hj_hHSPA5_I1, 1 μM jh_h+mHSP90B1_I2 and 5 μM TitB_hHSP90B1_O2. The human control primer mix with mouse outer primer O1 contained 5 μM TitA_mHspa5_O1 instead of 5 μM TitA_hHSPA5_O1, and the human control primer mix with mouse outer primer O2 contained 5 μM TitB_mHsp90b1_O2 instead of 5 μM TitB_hHSP90B1_O2. For assembly of mouse Hspa5 and Hsp90b1 transcript fragments, the primer mix contained 5 μM TitA_mHspa5_O1, 1 μM hj_mHspa5_I1, 1 μM jh_h+mHSP90B1_I2 and 5 μM TitB_mHsp90b1_O2. The mouse control primer mix with human outer primer O1 contained 5 μM TitA_hHSPA5_O1 instead of 5 μM TitA_mHspa5_O1, and the mouse control primer mix with human outer primer O2 contained 5 μM TitB_hHSP90B1_O2 instead of 5 μM TitB_mHsp90b1_O2. Thermal cycling was carried out in a MJ Research PTC-200 with calculated temperatures for 100 μl and with heated lid. Reverse transcription was carried out at 60° C. for 15 min, followed by inactivation of Reverse Transcriptase at 95° C. for 2 min, followed by specific amplification for 5 cycles with denaturation at 95° C. for 20 sec, touchdown annealing at 65° C. (−1° C. per cycle) for 30 sec and extension at 72° C. for 40 sec, followed by further amplification and annealing for 30 cycles with denaturation at 95° C. for 20 sec, annealing at 60° C. for 30 sec and extension at 72° C. for 40 sec, followed by final extension at 72° C. for 5 min. After addition of 3 μl 6×DNA Loading dye to 15 μl sample, the assembly products were separated on a 1.2% agarose gel in 1×TBE buffer to visualize the obtained products.

Figure 1:
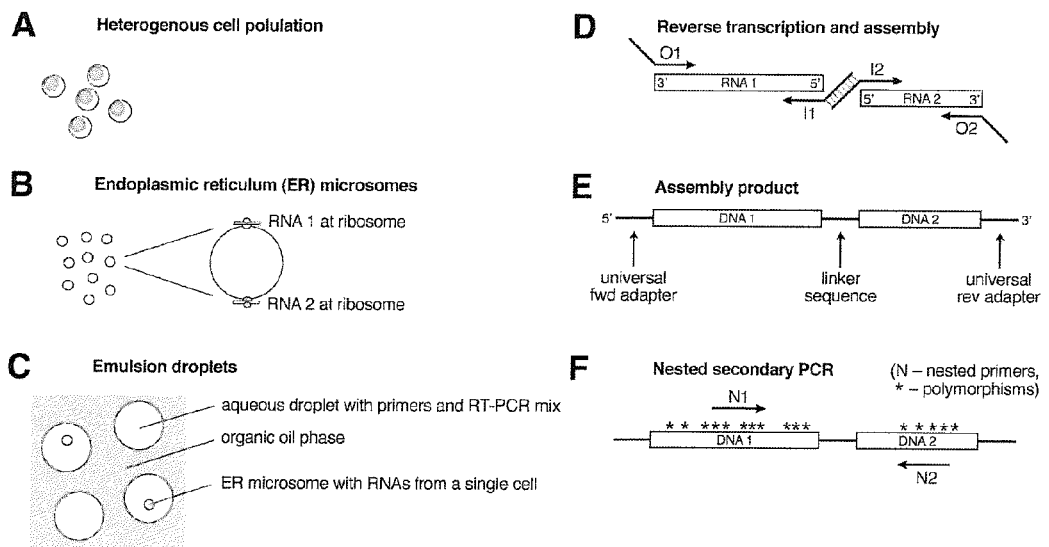
FIGS. 1A-1F: Amplification and linking of mRNA sequences by emulsion RT-PCR assembly from mixed human and mouse cells.
Figure 2:
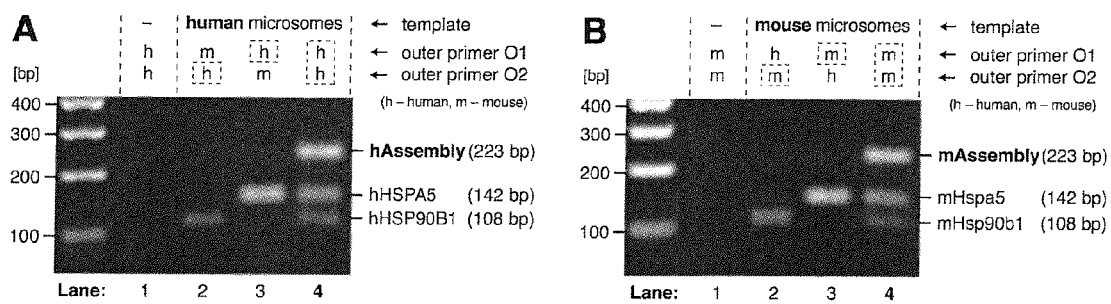

FIG. 2 shows that the human assembly product is only obtained from human ER microsomes when using the human-specific primers for the HSPA5 and HSP90B1 tran-

TABLE 1

List of primers for reverse transcription and clonally paired amplification from ER microsomes of human HEK 293T cells and mouse NIH/3T3 cells

| Primer name | Species-specificity | Sequence 5'->3' (gene-specific part in capital letters; species differences underlined) |
|---|---|---|
| TitA_hHSPA5_O1 | human only | cgtatcgcctccctcgcgccatcag TGATTGTCTTTTGTCAGGGGTCT (SEQ ID NO. 1) |
| TitA_mHspa5_O1 | mouse only | cgtatcgcctccctcgcgccatcag TGATTGTCTTTTGTTAGGGGTCG (SEQ ID NO. 2) |
| hj_hHSPA5_I1 | human only | tcgtgcctatatccttactgactctgc GGAACACAGTGGTGCCTACC (SEQ ID NO. 3) |
| hj_mHspa5_I1 | mouse only | tcgtgcctatatccttactgactctgc GGAACACTGTGGTACCCACC (SEQ ID NO. 4) |
| jh_h+mHSP90B1_I2 | human/mouse | gcagagtcagtaaggatataggcacga TCCAATTCAAGGTAATCAGATGC (SEQ ID NO. 5) |
| TitB_hHSP90B1_O2 | human only | ctatgcgccttgccagcccgctcag CCCAAGAGGAAACACTCTAGGAC (SEQ ID NO. 6) |
| TitB_mHsp90b1_O2 | mouse only | ctatgcgccttgccagcccgctcag CCCAAGAGGAAACACACTAGGTC (SEQ ID NO. 7) | script fragments (FIG. 2A). Similarly, the mouse assembly product is only obtained from mouse ER microsomes when using the mouse-specific primers for the Hspa5 and Hsp90b1 transcript fragments (FIG. 2B). We conclude that combinations of transcript fragments can be assembled and amplified in a cell type-specific way using the RT-PCR assembly set-up described here.

For clonally paired amplification of human and mouse transcript fragments from mixed human and mouse ER microsomes in emulsion RT-PCR, each ER microsome pellet was resuspended in 20 µl Wash buffer by pipetting 10 times up and down. A master mix (250 µl) was set up containing 1× Verso 1-Step PCR Master Mix (Thermo Scientific), 0.5 µg/µl BSA, 1× Verso Enzyme Mix (Thermo Scientific), 20 µl of the appropriate primer mix and 20 µl microsomes prepared from mixed (1:1) human HEK 293T and mouse NIH/3T3 cells. Primer sequences are listed in Table 1. The primer mix for amplification and assembly of human and mouse transcript fragments contained 2.5 µM TitA_hHSPA5_O1, 2.5 µM TitA_mHspa5_O1, 0.5 µM hj_hHSPA5_I1, 0.5 µM hj_mHspa5_I1, 1 µM jh_h+ mHSP90B1_I2, 2.5 µM TitB_hHSP90B 1_O2 and 2.5 µM TitB_mHsp90b1_O2. An aliquot of 50 µl of the master mix was transferred into one 250 µl tube of a PCR 8-strip on ice to carry out conventional open RT-PCR as a control in parallel. The remaining 200 µl of the master mix were gradually added (a 15 µl in 30 sec intervals) to 800 µl emulsion oil mix containing 4.5% (v/v) SPAN™ 80 (Sigma-Aldrich S6760), 0.4% (v/v) TWEEN™ 80 (Sigma-Aldrich P8074) and 0.05% (v/v) TRITON™ X-100 (Sigma-Aldrich T8787) in mineral oil (Sigma-Aldrich M5904) while stirring the oil mix on a magnetic stirrer (Gerhardt stirrer, speed 10). For emulsion RT-PCR, 600 µl of the resulting emulsion were transferred a 100 µl into six 250 µl tubes of a PCR 8-strip on ice while maintaining stirring of the emulsion. Thermal cycling of the open and emulsion RT-PCR reactions was carried out in a MJ Research PTC-200 with calculated temperatures for 100 µl and with heated lid. Reverse transcription was carried out at 60° C. for 15 min, followed by inactivation of Reverse Transcriptase at 95° C. for 2 min, followed by amplification for 5 cycles with denaturation at 95° C. for 20 sec, touchdown annealing at 65° C. (−1° C. per cycle) for 30 sec and extension at 72° C. for 40 sec, followed by further amplification and annealing for 5 cycles with denaturation at 95° C. for 20 sec, annealing at 60° C. for 30 sec and extension at 72° C. for 40 sec, followed by final extension at 72° C. for 5 min. An aliquot of 15 µl was taken from the open RT-PCR product, mixed with 3 µl 6×DNA Loading dye, frozen on dry ice and stored at −20° C. until use.

For DNA purification from the emulsion RT-PCR samples using a Zymo DNA CLEAN & CONCENTRATOR™-5 Kit (Zymo Research #D4013), the six 100 µl reactions were pooled a 300 µl into two fresh 2 ml centrifuge tubes, 1.2 ml isobutanol were added to each tube, and the solutions were vortexed shortly (~5 sec) until they became transparent. After addition of 300 µl Zymo DNA binding buffer and short vortexing (~5 sec), the solutions were centrifuged with 16,000 g for 1 min at room temperature, and 1.2 ml of the upper (organic) phases were removed. The remaining liquids were vortexed shortly (~5 sec), transferred to ZYMO-SPIN™ columns in collection tubes and centrifuged with 10,000 g for 30 sec at room temperature. The flow-throughs were discarded, 200 µl Zymo Wash buffer were added to each spin column, and centrifuged with 10,000 g for 30 sec at room temperature. After repeating the wash step once with 200 µl Wash buffer and once with 500 µl Wash buffer, the flow-throughs were discarded and the spin tubes centrifuged in empty collection tubes to get rid of remaining Wash buffer. The spin columns were transferred to fresh 1.5 ml centrifuge tubes and 8 µl nuclease-free water were added onto each column. After centrifugation with 10,000 g for 30 sec at room temperature, the eluted DNA samples were pooled into a fresh 1.5 ml centrifuge tube, mixed with 3 µl 6×DNA Loading dye, frozen on dry ice and stored at −20° C. until use. The assembly products from open and emulsion RT-PCR were run in parallel on a 1.2% agarose gel in 1×TBE buffer. After excision of agarose gel slices with the DNA in the 200-250 bp range (containing the assembled transcript fragments), the DNA was purified using a ZYMO-CLEAN™ Gel DNA Recovery Kit (Zymo Research D4007). After addition of 500 µl ADB buffer to the gel slices, the samples were incubated on a thermomixer at 50° C. for 10 minutes with 750 rpm shaking until the gel slices were completely dissolved. Each melted agarose solution was transferred to a spin column in a collection tube which was centrifuged at 10,000 g for 60 sec, washed two times by addition of 200 µl of Wash buffer and centrifugation at 10,000 g for 30 sec. followed by elution of the DNA with 15 µl of nuclease-free water. The 15 µl eluates were transferred into new 1.5 ml centrifuge tubes, frozen on dry ice and store at −20° C. until use.

The pairing combinations of the assembly products obtained in open RT-PCR and in emulsion RT-PCR were analyzed by secondary PCR amplification using four different mixes of nested primers representing the four possible combinations of the two assembled transcript fragments from human and mouse ER microsomes, namely human-human, human-mouse, mouse-human and mouse-mouse combination of the two genes. The semi-quantitative PCR was carried out in 60 µl reactions containing 65 mM Tris-Cl pH 8, 16.6 mM (NH4)2SO4, 3.1 mM MgCl2, 0.01% (v/v) Tween 20, 200 µM each dNTP, 0.14 U/µl Taq DNA polymerase, 1.5 µl gel-purified assembly product and 4 µl of the respective primer mix. Primer sequences are listed in Table 2.

TABLE 2

List of primers for nested amplification of specific pairings from transcript fragment assemblies

| Primer name | Species-specificity | Sequence 5'->3' (species differences underlined) | Tm [° C.] |
| --- | --- | --- | --- |
| hHSP90B1_n_fwd | human only | GGACGGGGAACGAC AATTACC (SEQ ID NO. 8) | 64.7 |
| mHsp90b1_n_fwd | mouse only | CACACTAGGTCGTG GAACAACAATTACT (SEQ ID NO. 9) | 64.5 |
| hHSPA5_n_rev | human only | AACAGTTGGTTGAT TATCAGAAGCTGTA GAA (SEQ ID NO. 10) | 65.2 |
| mHspa5_n_rev | mouse only | CTGATTATCGGAAGC CGTGGAG (SEQ ID NO. 11) | 65.1 |

The following four primer mixes were used: mouse-mouse (5 µM of each mHsp90b1_n_fwd and mHspa5_n_rev), mouse-human (5 µM of each mHsp90b1_n_fwd and hHSPA5_n_rev), human-mouse (5 µM of each hHSP90B1_n_fwd and mHspa5_n_rev) and human-human (5 µM of each hHSP90B1_n_fwd and hHSPA5_n_rev). Thermal cycling was carried out in a MJ Research PTC-200 with calculated temperatures for 60 µl and with heated lid. Initial denaturation was performed at 94° C. for 3 min, followed by 5 cycles with denaturation at 94° C. for 20 sec, touchdown annealing at 68° C. (−1° C. per cycle) for 30 sec and extension at 72° C. for 40 sec, followed by further amplification for 24 cycles with denaturation at 94° C. for 20 sec, annealing at 63° C. for 30 sec and extension at 72° C. for 40 sec, followed by final extension at 72° C. for 5 min. An aliquot of 12 µl was taken from each PCR product, mixed with 3 µl 6×DNA Loading dye, frozen on dry ice and stored at −20° C. until use. The nested PCR products were run on a 2% agarose gel in 1×TBE buffer to visualize the pairing combinations obtained from the RT-PCR assembly reactions.

FIG. 3 shows that all four possible combinations are strongly represented in the assemblies obtained by open RT-PCR (FIG. 3, upper panel). Also, it is visible that less transcripts were present in the mouse ER microsomes, resulting in slightly fainter bands (upper panel, lanes 1 and 2), probably because NIH/3T3 cells are smaller than HEK 293T cells and contain less transcripts. In contrast, two combinations of transcript pairing are strongly over-represented (>90% of total DNA) in the assemblies obtained by emulsion RT-PCR (FIG. 3, lower panel), namely the original pairing of mouse Hspa5 with mouse Hsp90b1 and the original pairing of human HSPA5 with human HSP90B1 (lower panel, lanes 1 and 4). We conclude that emulsion RT-PCR assembly from ER microsome transcripts results in strong enrichment of clonal pairings of endogenous transcript variants, representing the endogenous transcript pairing in the original cells.

Example 2

Determination of Combinations of Variable Sequence Regions on the Level of Single Cells Three different mouse hybridoma cell lines were obtained from the following sources: The hybridoma cell line 5E4/1F1 was obtained from Prof. Vladka Čurin Šerbec at the Blood Transfusion Centre of Slovenia in Ljubljana, and the hybridoma cell lines KT13 and KT22 developed by Kazumasa Takeda/Asako Sugimoto (Takeda et al. 2008) were obtained from the Developmental Studies Hybridoma Bank developed under the auspices of the NICHD and maintained by The University of Iowa, Department of Biology, Iowa City, Iowa 52242. Cells in suspension culture in 75 cm2 bottles were grown at 0.2-1 million cells/ml in DMEM medium (with 4.5 g/l glucose, Gibco #41966-052) with 15% FBS (Biochrom #S0615), 1× Penicillin/Streptomycin (Gibco #15140-122) and 1× GlutaMAX (Gibco #35050-038) at 37° C. in 5% CO2 and 92% relative humidity. Cycloheximide-treated frozen cell pellets were prepared from 0.5-1 million cells/ml as follows. Cycloheximide was added to the medium to 0.1 mg/ml final concentration, and the cells were incubated for 10 min at 37° C. Cells were pelleted by centrifugation with 180 g for 3 min at 4° C. and resuspended in cold PBS with 0.05 mg/ml cycloheximide at a concentration of 1 million cells per ml. The suspension was aliquoted à 1 ml in new 1.5 ml centrifuge tubes. After centrifugation with 180 g for 3 min at 4° C., the supernatant was removed, the cell pellets were snap-frozen in liquid nitrogen and stored at −80° C. until use.

For preparation of endoplasmic reticulum (ER) microsomes with associated mRNAs, frozen cell pellets of 1 million cells were resuspended in 120 µl cold MP HD buffer (25 mM HEPES-KOH pH 7.2, 110 mM KOAc, 5 mM Mg(OAc)2, 1 mM EGTA, 25% (w/w) sucrose, 5% (v/v) glycerol, 1 mM DTT, 1× Complete EDTA-free proteinase inhibitor cocktail, 0.1 mg/ml cycloheximide, 0.015% digitonin and 80 U/ml RNase Inhibitor [Ambion]). The suspension was pipetted up and down for 15 times to lyze the cells and incubated on ice for 5 min. The homogenate was split à 55 µl into fresh 1.5 ml centrifuge tubes and centrifuged with 600 g for 3 min at 4° C. to pellet nuclei and debris. The supernatants containing membranes and cytosol were transferred à 40 µl into fresh 1.5 ml centrifuge tubes, and the sucrose was diluted to 12-13% (w/w) by addition of 40 µl nuclease-free water to each tube. After mixing by pipetting 5 times up and down and 10 times tapping the tubes, ER microsomes were pelleted by centrifugation with 20,800 g for 90 min at 4° C. in an Eppendorf centrifuge 5810 R (rotor F-45-30-11). The supernatant (cytosol) was transferred into a fresh 1.5 ml tube on ice, frozen on dry ice and stored at −80° C. until use. The ER microsome pellets were resuspended in 90 µl Wash buffer (25 mM HEPES-KOH pH 7.2, 110 mM KOAc, 2.5 mM Mg(OAc)2, 1 mM EGTA, 1 mM DTT, 1× Complete EDTA-free proteinase inhibitor cocktail, 0.1 mg/ml cycloheximide, 0.004% digitonin and 80 U/ml RNase Inhibitor [Ambion]) by pipetting 10 times up and down. The ER microsomes were pelleted by centrifugation with 20,800 g for 45 min at 4° C. After removal of the supernatants, the ER microsome pellets were snap-frozen in liquid N2 and store at −80° C. until use.

As a first control experiment, we amplified and linked the immunoglobulin VL and VH sequences from ER microsomes of each hybridoma cell line separately. Each ER microsome pellet was resuspended in 20 µl Wash buffer by pipetting 10 times up and down. The 20 µl reaction mix for each sample was composed of 1× Verso 1-Step PCR Master Mix (Thermo Scientific), 0.5 µg/µl BSA, 1× Verso Enzyme Mix (Thermo Scientific), 1.6 µl primer mix and 2 µl microsomes from 5E4, KT13 or KT22 hybridoma cells, respectively. The primer sequences for specific amplification of mouse IgM heavy chain VH sequences and kappa light chain VL sequences were based on primers described before (Wang et al. 2000). Primer sequences are listed in Table 3.

TABLE 3

List of primers for reverse transcription and assembly of immunoglobulin VL and VH sequences from ER microsomes of mouse hybridoma cells, based on primers described before (Wang et al. 2000).

| Primer name | d-fold degeneracy1 | Sequence 5'->3' (gene-specific part in capital letters2) |
|---|---|---|
| O1_IgM | 1 | cgtatcgcctccctcgcgcc atcagGACATTTGGGAAGGA CTGACTCTC (SEQ ID NO. 12) |
| I1_5'MH1 | 128 | tcgtgcctatatccttactg actctgcSARGTNMAGCTGS AGSAGTC (SEQ ID NO. 13) |
| I2_5'Mk | 128 | gcagagtcagtaaggatata ggcacgaGAYATTGTGMTSA CMCARWCTMCA (SEQ ID NO. 14) |

TABLE 3-continued

List of primers for reverse transcription and assembly of immunoglobulin VL and VH sequences from ER microsomes of mouse hybridoma cells, based on primers described before (Wang et al. 2000).

| Primer name | d-fold degeneracy1 | Sequence 5'->3' (gene-specific part in capital letters2) |
|---|---|---|
| O2_3'Kc+1 | 1 | ctatgcgccttgccagcccg ctcagGGATACAGTTGGTGC AGCATCA (SEQ ID NO. 15) |

1with d being the number of unique sequences that are contained in the degenerate primer mix
2with base ambiguity codes: Y-pyrimidine (C or T), R-purine (A or G), W-weak (A or T), S-strong (G or C), K-keto (T or G), M-amino (C or A), D-A, G, T (not C), V-A, C, G (not T), H-A, C, T (not G), B-C, G, T (not A), N-any base The primer mix for amplification and assembly of immunoglubulin VH and VL transcript fragments contained 10 µM O1_IgM, 2 µM I1_5'MH1, 2 µM I2_5'Mk and 10 µM O2_3'Kc+1 (primer 3'Kc with additional A base at the 3' end). Thermal cycling was carried out in a MJ Research PTC-200 with calculated temperatures for 20 µl and with heated lid. Reverse transcription was carried out at 50° C. for 15 min, followed by inactivation of Reverse Transcriptase at 95° C. for 2 min, followed by amplification for 4 cycles with denaturation at 95° C. for 20 sec, rampdown annealing at 60-50° C. (−0.2° C./sec) for 50 sec and extension at 72° C. for 1 min, followed by an extension step at 72° C. for 1 min, followed by further amplification and annealing for 16 cycles with denaturation at 95° C. for 20 sec, annealing at 60° C. for 30 sec and extension at 72° C. for 1 min, followed by final extension at 72° C. for 5 min. Each 20 µl reaction product was mixed with 4 µl 6×DNA Loading dye, frozen on dry ice and stored at −20° C. until use.

The assembly products from the open RT-PCR were run in parallel on a 1.2% agarose gel in 1×TBE buffer. After excision of agarose gel slices with the DNA in the 800-950 bp range (containing the assembled transcript fragments), the DNA was purified using a ZYMOCLEAN™ Gel DNA Recovery Kit (Zymo Research #D4007). After addition of 500 µl ADB buffer to the gel slices, the samples were incubated on a thermomixer at 50° C. for 10 minutes with 750 rpm shaking until the gel slices were completely dissolved. Each melted agarose solution was transferred to a spin column in a collection tube which was centrifuged at 10,000 g for 60 sec, washed two times by addition of 200 µl of Wash buffer and centrifugation at 10,000 g for 30 sec, followed by elution of the DNA with 7 µl of nuclease-free water. The 7 µl eluates were transferred into new 1.5 ml centrifuge tubes, frozen on dry ice and store at −20° C. until use.

We used the assembled VL+VH sequences as templates for PCR to further amplify each seperate VL and VH sequence and each VL+VH assembly and visualize the parts and the complete assemblies by agarose gel electrophoresis. The PCR was carried out in 35 µµī reactions containing 1× PHUSION™ HF buffer (Finnzymes #F-530S), 200 µM each dNTP, 0.02 U/µl PHUSION™ high-fidelity DNA polymerase (Finnzymes #F-530S), 1.75 µµī or each primer mix (containing 10 µM of each primer), and gel-purified assembled DNA (0.75 µµī for amplification of seperate VL and VH, and 1.5 µµī for amplification of the assembled VL+VH sequence). Primer sequences are listed in Table 3 and Table 5.

TABLE 4

Primers for further amplification of assembled immunoglobulin VH and VL sequences. The outer adapter sequences (FLX Titanium primers) were taken from the Technical Bulletin for the Genome Sequencer FLX System, Series Lib-A Chemistry (Roche, August 2009)

| Primer name | Sequence 5'->3' |
|---|---|
| FLX_TitA_fwd | Cgtatcgcctccctcgcgccatcag (SEQ ID NO. 16) |
| FLX_TitB_rev | Ctatgcgccttgccagcccgctcag (SEQ ID NO. 17) |
| hj_fwd | Tcgtgcctatatccttactgactctgc (SEQ ID NO. 18) |
| jh_rev | Gcagagtcagtaaggatataggcacga (SEQ ID NO. 19) |

The following three primer mixes were used for PCR:
(1) jh_rev + FLX_TitB_rev (inner linker and outer adapter, for amplification of only VL)
(2) hj_fwd + FLX_TitA_fwd (inner linker and outer adapter, for amplification of only VH)
(3) FLX_TitA_fwd + FLX_TitB_rev (outer adapters, for amplification of VL + VH assemblies) (SEQ ID numbers are given above).

Thermal cycling was carried out in a MJ Research PTC-200 with calculated temperatures for 35 µl and with heated lid. Initial denaturation was performed at 98° C. for 30 sec, followed by 32 cycles with denaturation at 98° C. for 7 sec and annealing/extension at 71° C. for 30 sec, followed by final extension at 72° C. for 5 min. An aliquot of 16 µl was taken from each PCR product, mixed with 4 µl 6×DNA Loading dye, frozen on dry ice and stored at −20° C. until use. The PCR products were run on a 1.2% agarose gel in 1×TBE buffer to visualize the separate VL and VH chains and the assembly products.

FIG. 4 shows that all VL sequences could be amplified (lanes 1, 4 and 7), as all VH sequences (lanes 2, 5 and 8) and all assembly sequences (lanes 3, 6 and 9). All VL, VH and assembly sequences were also verified by subsequent Sanger sequencing (data not shown). We conclude that the RT-PCR assembly from ER microsomes using degenerate primers can be used to assembly and analyze the endogenous VL and VH pairing in antibody-producing cells.

For clonally paired amplification of immunoglobulin VH and VL sequences from mixed hybridoma ER microsomes in emulsion RT-PCR, each ER microsome pellet was resuspended in 20 µl Wash buffer by pipetting 10 times up and down. Mixtures of ER microsomes from different hybridoma cell lines were prepared by mixing 7.5 µl of microsomes from each 5E4, KT13 and KT22 (for a 1:1:1 mix) or 17.1 µl 5E4 microsomes, 4.3 µl KT13 microsomes and 1.1 µl KT22 microsomes (for a 16:4:1 mix). A master mix (250 µl) was set up containing 1× Verso 1-Step PCR Master Mix (Thermo Scientific), 0.5 µg/µl BSA, 100 µg/ml cycloheximide, 1× Verso Enzyme Mix (Thermo Scientific), 20 µl of the appropriate primer mix and 20 µl mixed microsomes (either 1:1:1 mix or 16:4:1 mix of microsomes from 5E4, KT13 and KT22 hybridoma cells, respectively). The primer sequences for specific amplification of mouse IgM heavy chain VH sequences and kappa light chain VL sequences were based on primers described before (Wang et al. 2000). Primer sequences are listed in Table 5.

TABLE 5

List of primers for reverse transcription and clonally paired amplification from ER microsomes of mouse hybridoma cells, based on primers described before (Wang et al. 2000)

| Primer name | d-fold degen- eracy1 | Sequence 5'->3' (10 bp multiplexing IDs2 shown as - {MID}-; gene-specific part in capital letters3) |
|---|---|---|
| O1_MID_IgM | 1 | cgtatcgcctccctcgcgccatcag-{MID1/3}-GACATTTGGGAAGGACT GACTCTC (SEQ ID NO. 20) |
| I1_MID_5' MH1 | 128 | tcgtgcctatatccttactgactctg cSARGTNMAGCTGSAGSAGTC (SEQ ID NO. 21) |
| I2_MID_5' Mk | 128 | gcagagtcagtaaggatataggcacg aGAYATTGTGMTSACMCARWCTMCA (SEQ ID NO. 22) |
| O2_MID_3' Kc+1 | 1 | ctatgcgccttgccagcccgctcag-{MID12/14}-GGATACAGTTGGTGC AGCATCA (SEQ ID NO. 23) |

1with d being the number of unique sequences that are contained in the degenerate primer mix
2with MID sequences taken from the Technical Bulletin for the Genome Sequencer FLX System, Series Lib-A Chemistry (Roche, August 2009): MIDI-ACGAGTGCGT, MID3-AGACGCACTC, MID12-TACT-GAGCTA, MID14-CGAGAGATAC.
3with base ambiguity codes: Y-pyrimidine (C or T), R-purine (A or G), W-weak (A or T), S-strong (G or C), K-keto (T or G), M-amino (C or A), D-A, G, T (not C), V-A, C, G (not T), H-A, C, T (not G), B-C, G, T (not A), N-any base The primer mix for amplification and assembly of immunoglobulin VH and VL transcript fragments contained 10 µM O1 MIDJgM, 2 µM 11 5'MH1, 2 µM I2_5'Mk and 10 µM 02_MID_3' c+1 (primer 3'Kc with additional A base at the 3' end). For the 1:1:1 microsome mix, the MIDI multiplexing ID was used in the 01_MID_IgM primer, and the MID12 multiplexing ID sequence was used in the 02_MID_3"Kc+1 primer. For the 16:4:1 microsome mix, the MID3 multiplexing ID was used in the 01_MID_IgM primer, and the MID 14 multiplexing ID sequence was used in the 02_MID_3'Kc+1 primer. An aliquot of 50 µl of the master mix was transferred into one 250 µl tube of a PCR 8-strip on ice to carry out conventional open RT-PCR as a control in parallel. The remaining 200 µl of the master mix were gradually added (a 15 µl in 30 sec intervals) to 800 µl emulsion oil mix containing 4.5% (v/v) SPAN™ 80 (Sigma-Aldrich S6760), 0.4% (v/v) TWEEN™ 80 (Sigma-Aldrich P8074) and 0.05% (v/v) TRITON™ X-100 (Sigma-Aldrich T8787) in mineral oil (Sigma-Aldrich M5904) while stirring the oil mix on a magnetic stirrer (Gerhardt stirrer, speed 10). For emulsion RT-PCR, 600 µl of the resulting emulsion were transferred a 100 µl into six 250 µl tubes of a PCR 8-strip on ice while maintaining stirring of the emulsion. Thermal cycling of the open and emulsion RT-PCR reactions was carried out in a MJ Research PTC-200 with calculated temperatures for 100 µl and with heated lid. Reverse transcription was carried out at 50° C. for 15 min, followed by inactivation of Reverse Transcriptase at 95° C. for 2 min, followed by amplification for 4 cycles with denaturation at 95° C. for 20 sec, rampdown annealing at 60-50° C. (−0.2° C./sec) for 50 sec and extension at 72° C. for 1 min, followed by an extension step at 72° C. for 1 min, followed by further amplification and annealing for 16 cycles with denaturation at 95° C. for 20 sec, annealing at 60° C. for 30 sec and extension at 72° C. for 1 min, followed by final extension at 72° C. for 5 min. An aliquot of 16 µl was taken from the open RT-PCR product, mixed with 4 µl 6×DNA Loading dye, frozen on dry ice and stored at −20° C. until use.

For DNA purification from the emulsion RT-PCR samples using a Zymo DNA CLEAN & CONCENTRATOR™-5 Kit (Zymo Research D4013), the six 100 µl reactions were pooled a 300 µl into two fresh 2 ml centrifuge tubes, 1.2 ml isobutanol were added to each tube, and the solutions were vortexed shortly (~5 sec) until they became transparent. After addition of 300 µl Zymo DNA binding buffer and short vortexing (~5 sec), the solutions were centrifuged with 16,000 g for 1 min at room temperature, and 1.2 ml of the upper (organic) phases were removed. The remaining liquids were vortexed shortly (~5 sec), transferred to ZYMO-SPIN™ columns in collection tubes and centrifuged with 10,000 g for 30 sec at room temperature. The flow-throughs were discarded, 200 µl Zymo Wash buffer were added to each spin column, and centrifuged with 10,000 g for 30 sec at room temperature. After repeating the wash step once with 200 µl Wash buffer and once with 500 µl Wash buffer, the flow-throughs were discarded and the spin tubes centrifuged in empty collection tubes to get rid of remaining Wash buffer. The spin columns were transferred to fresh 1.5 ml centrifuge tubes and 8 µl nuclease-free water were added onto each column. After centrifugation with 10,000 g for 30 sec at room temperature, the eluted DNA samples were pooled into a fresh 1.5 ml centrifuge tube, mixed with 3 µl 6×DNA Loading dye, frozen on dry ice and stored at −20° C. until use. The assembly products from open and emulsion RT-PCR were run in parallel on a 1.2% agarose gel in 1×TBE buffer. After excision of agarose gel slices with the DNA in the 800-950 bp range (containing the assembled transcript fragments), the DNA was purified using a ZYMO-CLEAN™ Gel DNA Recovery Kit (Zymo Research #D4007). After addition of 500 µl ADB buffer to the gel slices, the samples were incubated on a hermomixer at 50° C. for 10 minutes with 750 rpm shaking until the gel slices were completely dissolved. Each melted agarose solution was transferred to a spin column in a collection tube which was centrifuged at 10,000 g for 60 sec, washed two times by addition of 200 µl of Wash buffer and centrifugation at 10,000 g for 30 sec. followed by elution of the DNA with 10 µl of nuclease-free water. The 10 µl eluates were transferred into new 1.5 ml centrifuge tubes, frozen on dry ice and store at −20° C. until use.

The assembled DNA sequences from emulsion RT-PCR and from open RT-PCR were amplified in parallel by an intermediate PCR to obtain more material for further analysis. The PCR was carried out in 50 µl reactions containing 1× Phusion HF buffer (Finnzymes #F-530S), 200 µM each dNTP, 0.02 U/µl Phusion high-fidelity DNA polymerase (Finnzymes #F-530S), 5 µµî gel-purified assembly product and 0.5 µM of each primer FLX_TitA_fwd and FLX_Tit-B_rev. Thermal cycling was carried out in a MJ Research PTC-200 with calculated temperatures for 50 µl and with heated lid. Initial denaturation was performed at 98° C. for 30 sec, followed by 15 cycles with denaturation at 98° C. for 7 sec and annealing/extension at 72° C. for 30 sec, followed by final extension at 72° C. for 5 min. The amplified DNA assemblies were purified using a Zymo DNA CLEAN & CONCENTRATOR™-5 Kit (Zymo Research #D40 3). After addition of 300 µl Zymo DNA binding buffer and short vortexing (~5 sec), the samples were transferred to ZYMO-SPIN™ columns in collection tubes and centrifuged with 10,000 g for 30 sec at room temperature. The flow-throughs were discarded, 200 µl Zymo Wash buffer were added to each spin column, and centrifuged with 10,000 g for 30 sec at room temperature. After repeating the wash step once with 200 µl Wash buffer, the flow-throughs were discarded and the spin tubes centrifuged in empty collection tubes to get rid of remaining Wash buffer. The spin columns were transferred to fresh 1.5 ml centrifuge tubes and 10 µl nuclease-free water were added onto each column. After centrifugation with 10,000 g for 30 sec at room temperature, the eluted DNA samples were transferred to fresh 1.5 ml centrifuge tubes, diluted to 20 µl with nuclease-free water, frozen on dry ice and stored at −20° C. until use.

The pairing combinations of the assembly products obtained in open RT-PCR and in emulsion RT-PCR were analyzed by semi-quantitative PCR amplification using nine different mixes of nested primers representing the nine possible combinations of the assembled transcript fragments from the three hybridoma cell lines. The semi-quantitative PCR was carried out in 50 µl reactions containing 1× PHUSION™ HF buffer (Finnzymes #F-530S), 200 µM each dNTP, 0.02 U/µl PHUSION™ high-fidelity DNA polymerase (Finnzymes #F-530S), 1 µl purified assembly product from intermediate amplification and 2.5 µl of the respective primer mix (a mix containing 10 µM each primer). Primer sequences are listed in Table 6.

TABLE 6

List of primers for nested amplification of specific pairings of assembled immunoglobulin VH and VL sequences from hybridoma cell lines 5E4, KT13 and KT22

| Primer name | Primer name | Sequence 5'->3' (differences between hybridoma cell lines underlined) | Tm [° C.] |
|---|---|---|---|
| VL_5E4 | VL_5E4 | GATCTGCAAGAGATGGAGGCTTGA (SEQ ID NO. 24) | 66.2 |
| VL_KT13 | VL_KT13 | CCTGCAGGTCATGGTGACCTTT (SEQ ID NO. 25) | 65.7 |
| VL_KT22 | VL_KT22 | GCATGGCAAGTGATGCTGACTG (SEQ ID NO. 26) | 66.4 |
| VH_5E4 | VH_5E4 | GCGGACCCAGTTCATCCAGTAGT (SEQ ID NO. 27) | 65.8 |
| VH_KT13 | VH_KT13 | TGTTTTACCCAGTGCATCCAGTAGG (SEQ ID NO. 28) | 65.3 |
| VH_KT22 | VH_KT22 | CGAACCCAAGACATGGCATAGC (SEQ ID NO. 29) | 66.0 |

The following nine primer mixes were used for nested PCR:
VL_5E4 + VH_5E4 (endogenous combination in 5E4 cells)
VL_5E4 + VH_KT13
VL_5E4 + VH_KT22
VL_KT13 + VH_5E4
VL_KT13 + VH_KT13 (endogenous combination in KT13 cells)
VL_KT13 + VH_KT13
VL_KT22 + VH_5E4
VL_KT22 + VH_KT13
VL_KT22 + VH_KT22 (endogenous combination in KT22 cells)

Thermal cycling was carried out in a MJ Research PTC-200 with calculated temperatures for 50 µl and with heated lid. Initial denaturation was performed at 98° C. for 30 sec, followed by 24 cycles with denaturation at 98° C. for 7 sec and annealing/extension at 72° C. for 30 sec, followed by final extension at 72° C. for 5 min. An aliquot of 15 µl was taken from each PCR product, mixed with 3 µl 6×DNA Loading dye, frozen on dry ice and stored at −20° C. until use. The nested PCR products were run on a 1.2% agarose gel in 1×TBE buffer to visualize the pairing combinations obtained from the RT-PCR assembly reactions.

FIG. 5 shows that all nine possible combinations are represented in the assemblies obtained by open RT-PCR (FIG. 5, upper panel). Also, it is visible that less transcripts were present in the KT22 ER microsomes, or the degenerate primers amplify these sequences not as good as those of 5E4 and KT13, resulting in fainter bands for KT22 (upper panel, lanes 7 to 9). In contrast, three combinations of transcript pairing are strongly over-represented (>95% of total DNA) in the assemblies obtained by emulsion RT-PCR (FIG. 5, lower panel), namely the original pairing of the endogenous VL and VH sequences (lower panel, lanes 1, 5 and 9). We conclude that emulsion RT-PCR assembly from ER microsomes results in strong enrichment of clonal pairings of endogenous transcript variants, representing the endogenous transcript pairing in the antibody-producing hybridoma cells.

Example 3

Determination of Combinations of Variable Sequence Regions from Complex Human Lymphocyte Populations Lymphocytes (B cells or T cells) from human blood or other human tissues such as bone marrow, thymus or spleen are enriched or isolated using a suitable protocol or a commercially available kit. For example, the RosetteSep Human B Cell Enrichment Cocktail (Stemcell Technologies #15024) is used for isolation of untouched human B cells from whole blood, or the ROSETTESEP™ Human T Cell Enrichment Cocktail (Stemcell Technologies #15021) is used for isolation of untouched human T cells from whole blood. After microsome preparation was performed as described, clonal assembly and amplification of variable sequence regions is performed by emulsion PGR from the microsomes using suitable primer sets.

For example, the ROSETTESEP™ Human B Cell Enrichment Cocktail (Stemcell Technologies #15024) is used for isolation of untouched human B cells from whole blood. The isolated B cells are resuspended in DMEM medium and treated with cycloheximide (0.1 mg/ml final concentration) for 10 min at 37° C. to arrest translating mRNAs at the endoplasmic reticulum. Cells are pelleted by centrifugation with 180 g for 3 min at 4° C. and resuspended in cold PBS with 0.05 mg/ml cycloheximide at a concentration of 1 million cells per ml. The suspension is aliquoted a 1 ml in new 1.5 ml centrifuge tubes. After centrifugation with 180 g for 3 min at 4° C., the supernatant is removed, the cell pellets are snap-frozen in liquid nitrogen and stored at −80° C. until use. Microsomes are prepared as described above in "Example 2: Determination of combinations of variable sequence regions on the level of single cells".

For clonally paired assembly and amplification of human immunoglobulin heavy chain and light chain sequences from human B cell microsomes in emulsion RT-PCR, each microsome pellet is resuspended in 20 µl Wash buffer by pipetting 10 times up and down. A master mix (250 µl) is set up containing 1× Verso 1-Step PCR Master Mix (Thermo Scientific), 0.5 µg/µl BSA, 100 µg/ml cycloheximide, 1× Verso Enzyme Mix (Thermo Scientific), 20 µl of the appropriate primer mix and 20 µl B cell microsomes. Different primer sets have been described before for specific amplification of human immunoglobulin variable sequences, which can be adapted for the method described here. One exemplary primer set is listed below for reverse transcription, clonal assembly and amplification of human IgM heavy chain and kappa light chain sequences, including suitable overlap sequences for PCR overlap extension as well as outer adapter sequences for subsequent amplification and next generation sequencing on the Roche GS FLX+ system for 800-1000 base reads. Other overlap sequences and adapter sequences can be used to accommodate the procedure to alternative suitable sequencing systems. For example, a primer set is used for human immunoglobulin sequences that consists of the following subsets:

one IgM heavy chain constant region reverse primer modified from Wang et al. 2000 to match the homologous human transcript sequence, fused to 5' adapter sequences compatible with the Roche GS FLX+ system;

six heavy chain variable region forward primers modified from Briney et al. 2012, fused to 5' overlap sequences for assembly by overlap extension;

four kappa light chain variable region forward primers modified from Lim et al. 2010, fused to 5' overlap sequences for assembly by overlap extension;

one kappa light chain constant region reverse primer modified from Wang et al. 2000 to match the homologous human transcript sequence, fused to 5' adapter sequences compatible with the Roche GS FLX+ system.

Primer sequences are listed in Table 7.

TABLE 7

List of primers for reverse transcription and clonally paired amplification from microsomes of human B cells.

| Primer name | Sequence 5'->3'; exemplary multiplexing identifiers (MID) underlined; gene-specific part in capital letters[1] |
|---|---|
| O1_MID1_IgMc_Wang | cgtatcgcctccctcgcgccatcag<u>acga</u><br><u>gtgcgt</u>AAGGGTTGGGGCGGATGCACTCC<br>(SEQ ID NO. 30) |
| I1_hj_VH17_Briney | tcgtgcctatatccttactgactctgcGG<br>CCTCAGTGAAGGTCTCCTGCAAG<br>(SEQ ID NO. 31) |
| I1_hj_VH2_Briney | tcgtgcctatatccttactgactctgcGT<br>CTGGTCCTACGCTGGTGAACCC<br>(SEQ ID NO. 32) |
| I1_hj_VH3_Briney | tcgtgcctatatccttactgactctgcCT<br>GGGGGGTCCCTGAGACTCTCCTG<br>(SEQ ID NO. 33) |
| I1_hj_VH4_Briney | tcgtgcctatatccttactgactctgcCT<br>TCGGAGACCCTGTCCCTCACCTG<br>(SEQ ID NO. 34) |
| I1_hj_VH5_Briney | tcgtgcctatatccttactgactctgcCG<br>GGGAGTCTCTGAAGATCTCCTGT<br>(SEQ ID NO. 35) |
| I1_hj_VH6_Briney | tcgtgcctatatccttactgactctgcTC<br>GCAGACCCTCTCACTCACCTGTG<br>(SEQ ID NO. 36) |
| I2_jh_VK1_Lim | gcagagtcagtaaggatataggcacgaGA<br>CATCCRGDTGACCCAGTCTCC<br>(SEQ ID NO. 37) |
| I2_jh_VK246_Lim | gcagagtcagtaaggatataggcacgaGG<br>GATATTGTGMTGACYCAGWCTCC<br>(SEQ ID NO. 38) |
| I2_jh_VK3_Lim | gcagagtcagtaaggatataggcacgaGG<br>AGAAATTGTRWTGACRCAGTCTCC<br>(SEQ ID NO. 39) |
| I2_jh_VK5_Lim | gcagagtcagtaaggatataggcacgaGC<br>AGAAACGACACTCACGCAGTCTC<br>(SEQ ID NO. 40) |
| O2_MID12_IgKc_Wang | ctatgcgccttgccagcccgctcag<u>tact</u><br><u>gagcta</u>GAAGACAGATGGTGCAGCCACAG<br>TTC<br>(SEQ ID NO. 41) |

[1]with base ambiguity codes: Y-pyrimidine (C or T), R-purine (A or G), W-weak (A or T), M-amino (C or A), D-A, G, T (not C)

The primer mix for amplification and assembly of human immunoglobulin VH and VL transcript fragments contains 5 µM 01_MID1_IgMc_Wang, 0.17 µM of each of the six I1_hj_VH_Briney primers, 0.25 µM of each of the four I2Jh_V_Lim primers and 5 µM 02_MID12_IgKc_Wang. Clonally paired amplification of human VH and VL sequences from human B cell microsomes in emulsion RT-PCR is carried out as described above in "Example 2: Determination of combinations of variable sequence regions on the level of single cells", with the following modified thermal cycling conditions: Reverse transcription is carried out at 54° C. for 30 min, followed by inactivation of Reverse Transcriptase at 95° C. for 2 min, followed by amplification for 6 cycles with denaturation at 95° C. for 20 sec, annealing at 55° C. for 40 sec and extension at 72° C. for 1:30 min, followed by an extension step at 72° C. for 2 min, followed by further amplification and annealing for 10 cycles with denaturation at 95° C. for 20 sec, annealing at 60° C. for 40 sec and extension at 72° C. for 1:30 min, followed by final extension at 72° C. for 5 min. Size selection of the assemblies is carried out by agarose gel electrophoresis and excision of the 750-900 bp range, followed by DNA recovery from the gel piece (ZYMOCLEAN™ Gel DNA recovery kit, Zymo Research # D4007) and subsequent further amplification of the DNA by emulsion PCR using the Micellula emulsion kit (EURx #3600) with PHUSION™ high-fidelity DNA polymerase (New England Biolabs # M0530S), followed by further purification of the DNA using size selection on agarose gel as described and/or a PCR purification system, for example Agencourt AMPURE™ XP PCR Purification (Beckman Coulter # A63880).

The amplified and purified DNA assemblies can then be subjected to high-throughput nucleic acid sequencing methods to determine the paired sequences derived from individual B cells. FIG. 6 shows an exemplary agarose gel picture of a complex mixture of assembled human immunoglobulin heavy and light chains.

The invention claimed is:

1. A method for linking at least two target mRNA molecules from an endoplasmic reticulum, comprising the steps of:
   a. isolating a fraction from a sample, wherein the fraction comprises the endoplasmic reticulum comprising at least two target mRNA molecules, such that the endoplasmic reticulum organelles are collapsed into endoplasmic reticulum microsomes through treatment with buffers containing detergents;
   b. diluting said fraction and
      i. aliquoting the dilution in multiple separate reaction vessels such that each reaction vessel comprises a maximum of one endoplasmic reticulum microsome, or
      ii. encapsulating said endoplasmic reticulum microsome in emulsion droplets such that each droplet comprises an a maximum of one endoplasmic reticulum microsome, and
   c. linking said at least two target mRNA molecules, wherein the at least two target mRNA molecules are sequences encoding variable heavy chain (VH) domains and variable light chain (VL) domains or sequences encoding T cell receptor alpha and beta chains.

2. The method according to claim 1, further comprising the step of:
   a. determining the nucleic acid sequence of at least a portion of said linked target mRNA molecules or
   b. rearranging and/or subcloning said linked target mRNA molecules for phenotypic or functional analyses or
   c. in vitro translating said linked target mRNA molecules.

3. The method according to claim 1, wherein the linking step is done by means of a method selected from the group of:
   a. nucleic acid amplification,
   b. polymerase chain reaction amplification,
   c. site-specific recombination,
   d. ligation and
   e. tagging of the target mRNA molecules with a nucleic acid barcode sequence.

4. The method according to claim 2, wherein said determining the nucleic acid sequence step is done by sequencing.

5. The method of claim 4, wherein the sequencing is next generation sequencing.

6. The method according to claim 5, wherein the next generation sequencing is done by a method selected from the group of:
   a. sequencing by synthesis,
   b. pyrosequencing,
   c. sequencing by oligo ligation,
   d. semiconductor technology and
   e. single molecule real-time sequencing.

7. The method according to claim 2, wherein said rearranging and/or subcloning step is done by a method selected from the group of assembly by overlap extension polymerase chain reaction, site-specific recombination, and/or ligation.

8. The method according to claim 2, wherein said in vitro translating step is done by cell-free in vitro translation.

9. The method according to claim 1, wherein the endoplasmic reticulum is morphologically and/or spatially segregated by a membrane.

10. The method according to claim 1, wherein the target mRNA molecules are enclosed in a membrane or associated with a membrane.

11. The method according to claim 1, wherein the target mRNA encode VL and/or VH domains and the linking is performed using primers comprising any of SEQ ID NOs 1-41.

\* \* \* \* \*